(12) United States Patent
Kobayashi et al.

(10) Patent No.: US 9,181,348 B2
(45) Date of Patent: Nov. 10, 2015

(54) PHARMACEUTICAL COMPOSITION FOR TREATMENT AND/OR PROPHYLAXIS OF CANCER

(75) Inventors: Shinichi Kobayashi, Kamakura (JP); Fumiyoshi Okano, Kamakura (JP); Takanori Saito, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 14/236,665

(22) PCT Filed: Aug. 3, 2012

(86) PCT No.: PCT/JP2012/069842
§ 371 (c)(1),
(2), (4) Date: Feb. 3, 2014

(87) PCT Pub. No.: WO2013/018889
PCT Pub. Date: Feb. 7, 2013

(65) Prior Publication Data
US 2014/0178373 A1    Jun. 26, 2014

(30) Foreign Application Priority Data

Aug. 4, 2011 (JP) ................................. 2011-171379

(51) Int. Cl.
| | | |
|---|---|---|
| C07K 16/30 | (2006.01) | |
| C07K 16/28 | (2006.01) | |
| A61K 39/395 | (2006.01) | |
| A61K 45/06 | (2006.01) | |
| A61K 47/48 | (2006.01) | |
| A61K 39/00 | (2006.01) | |

(52) U.S. Cl.
CPC ........... *C07K 16/30* (2013.01); *A61K 39/39558* (2013.01); *A61K 45/06* (2013.01); *A61K 47/48569* (2013.01); *A61K 47/48584* (2013.01); *A61K 47/48592* (2013.01); *A61K 47/48607* (2013.01); *A61K 47/48623* (2013.01); *A61K 47/48638* (2013.01); *C07K 16/28* (2013.01); *A61K 2039/505* (2013.01); *C07K 2317/24* (2013.01); *C07K 2317/732* (2013.01)

(58) Field of Classification Search
CPC ............ C07K 16/30; C07K 16/3015–16/3069; C07K 16/461–16/467; A61K 39/395; A61K 39/39558
See application file for complete search history.

(56) References Cited

U.S. PATENT DOCUMENTS

| | | | |
|---|---|---|---|
| 5,698,396 A | 12/1997 | Pfreundschuh | |
| 6,335,170 B1 | 1/2002 | Orntoft | |
| 6,444,425 B1 | 9/2002 | Reed et al. | |
| 7,449,184 B2 | 11/2008 | Allison et al. | |
| 7,485,302 B2 | 2/2009 | Adams et al. | |
| 7,745,391 B2 | 6/2010 | Mintz et al. | |
| 8,211,634 B2 | 7/2012 | Depinho et al. | |
| 8,709,418 B2 | 4/2014 | Okano et al. | |
| 8,828,398 B2 | 9/2014 | Kobayashi et al. | |
| 8,911,740 B2 | 12/2014 | Saito et al. | |
| 2002/0006404 A1 | 1/2002 | Hanna et al. | |
| 2003/0118599 A1 | 6/2003 | Algate et al. | |
| 2003/0190640 A1 | 10/2003 | Faris et al. | |
| 2004/0029114 A1 | 2/2004 | Mack et al. | |
| 2004/0236091 A1 | 11/2004 | Chicz et al. | |
| 2004/0258678 A1 | 12/2004 | Bodary et al. | |
| 2005/0003390 A1 | 1/2005 | Axenovich et al. | |
| 2005/0032113 A1 | 2/2005 | Tanaka et al. | |
| 2005/0244413 A1 | 11/2005 | Adolf et al. | |
| 2006/0019256 A1 | 1/2006 | Clarke et al. | |
| 2006/0069054 A1 | 3/2006 | Houghton et al. | |
| 2006/0275305 A1 | 12/2006 | Bryant | |
| 2007/0048301 A1 | 3/2007 | Bodary-Winter et al. | |
| 2007/0154931 A1 | 7/2007 | Radich et al. | |
| 2007/0264253 A1 | 11/2007 | Liu et al. | |

(Continued)

FOREIGN PATENT DOCUMENTS

| | | |
|---|---|---|
| CN | 1705676 A | 12/2005 |
| CN | 101120252 A | 2/2008 |
| CN | 101189516 A | 5/2008 |
| CN | 102170907 A | 8/2011 |
| EP | 2 325 648 A1 | 5/2011 |
| EP | 2322221 A1 | 5/2011 |
| EP | 2 532 367 A1 | 12/2012 |
| EP | 2 532 743 A1 | 12/2012 |
| EP | 2 832 365 A1 | 2/2015 |
| EP | 2 832 366 A1 | 2/2015 |

(Continued)

OTHER PUBLICATIONS

GenBank Accession No. AAU93399, Sep. 22, 2005.

(Continued)

*Primary Examiner* — Sheela J Huff
*Assistant Examiner* — Jessica H Roark
(74) *Attorney, Agent, or Firm* — Birch, Stewart, Kolasch & Birch, LLP

(57) ABSTRACT

An object of the present invention is to prepare an antibody that targets CAPRIN-1 specifically expressed on the surface of cancer cells and is superior in antitumor activity to conventional antibodies and to provide use of the antibody as a therapeutic and/or preventive agent for cancer. The present invention provides use of an antibody targeting an identified cancer antigenic protein specifically expressed on the surface of cancer cells as a therapeutic and/or preventive agent for cancer, specifically, a pharmaceutical composition for treatment and/or prevention of cancer, comprising as an active ingredient an antibody or a fragment thereof which has immunological reactivity with a CAPRIN-1 protein, the antibody or the fragment thereof comprising a heavy chain variable region comprising amino acid sequences represented by SEQ ID NOs: 5, 6, and 7 and a light chain variable region comprising amino acid sequences represented by SEQ ID NOs: 9, 10, and 11.

18 Claims, No Drawings

(56) References Cited

U.S. PATENT DOCUMENTS

| | | |
|---|---|---|
| 2008/0075722 A1 | 3/2008 | DePinho et al. |
| 2008/0107668 A1 | 5/2008 | Philip et al. |
| 2010/0068724 A1 | 3/2010 | Fung et al. |
| 2011/0123492 A1 | 5/2011 | Okano et al. |
| 2011/0136121 A1 | 6/2011 | Okano et al. |
| 2011/0189700 A1 | 8/2011 | Moses et al. |
| 2011/0256144 A1 | 10/2011 | Okano et al. |
| 2012/0171699 A1 | 7/2012 | Goodman et al. |
| 2012/0214975 A1 | 8/2012 | Sandig et al. |
| 2012/0294860 A1 | 11/2012 | Ido et al. |
| 2012/0301471 A1 | 11/2012 | Kobayashi et al. |
| 2012/0301476 A1 | 11/2012 | Okano et al. |
| 2012/0321641 A1 | 12/2012 | Okano et al. |
| 2013/0045210 A1 | 2/2013 | Kobayashi et al. |
| 2013/0071398 A1 | 3/2013 | Saito et al. |

FOREIGN PATENT DOCUMENTS

| | | |
|---|---|---|
| JP | 2002-540790 A | 12/2002 |
| JP | 2003-528587 A | 9/2003 |
| JP | 2006-216040 A | 11/2006 |
| JP | 2013-502205 A | 1/2013 |
| JP | 2013-505028 A | 2/2013 |
| RU | 2234942 C2 | 2/2003 |
| RU | 2306952 C2 | 9/2007 |
| RU | 2006137060 A | 4/2008 |
| WO | WO 00/04149 A2 | 1/2000 |
| WO | WO 00/60077 A2 | 10/2000 |
| WO | WO 01/32910 A2 | 5/2001 |
| WO | WO 01/72295 A2 | 10/2001 |
| WO | WO 02/078524 A2 | 10/2002 |
| WO | WO 02/083070 A2 | 10/2002 |
| WO | WO 02/092001 A2 | 11/2002 |
| WO | WO 2004/076682 A2 | 9/2004 |
| WO | WO 2004/097051 A2 | 11/2004 |
| WO | WO 2005/007830 A2 | 1/2005 |
| WO | WO 2005/100998 A2 | 10/2005 |
| WO | WO 2005/116076 A2 | 12/2005 |
| WO | WO 2006/002378 A2 | 1/2006 |
| WO | WO 2007/150077 A2 | 12/2007 |
| WO | WO 2008/031041 A2 | 3/2008 |
| WO | WO 2008/059252 A2 | 5/2008 |
| WO | WO 2008/073162 A2 | 6/2008 |
| WO | WO 2008/088583 A2 | 7/2008 |
| WO | WO 2009/113742 A1 | 9/2009 |
| WO | WO 2010/016525 A1 | 2/2010 |
| WO | WO 2010/016526 A1 | 2/2010 |
| WO | WO 2010/016527 A1 | 2/2010 |
| WO | WO 2011/096517 A1 | 8/2011 |
| WO | WO 2011/096528 A1 | 8/2011 |
| WO | WO 2011/096534 A1 | 8/2011 |
| WO | WO 2011/096535 A1 | 8/2011 |
| WO | WO 2011/097533 A1 | 8/2011 |
| WO | WO 2013/018885 A1 | 2/2013 |
| WO | WO 2013/018886 A1 | 2/2013 |
| WO | WO 2013/018894 A1 | 2/2013 |
| WO | WO 2013/147169 A1 | 10/2013 |
| WO | WO 2013/147176 A1 | 10/2013 |

OTHER PUBLICATIONS

GenBank Accession No. BAF96513, Jan. 5, 2008.
GenBank Accession No. NM_001031365, Sep. 25, 2007.
GenBank Accession No. NM_001076062, Feb. 9, 2008.
GenBank Accession No. NM_001111289, Feb. 11, 2008.
GenBank Accession No. NM_001111290, Feb. 11, 2008.
GenBank Accession No. NM_001111291, Feb. 10, 2008.
GenBank Accession No. NM_001111292, Feb. 11, 2008.
GenBank Accession No. NM_016739, Feb. 10, 2008.
GenBank Accession No. NM_05898, Feb. 11, 2008.
GenBank Accession No. NM_203364, Feb. 10, 2008.
GenBank Accession No. Q14444, Jun. 10, 2008.
GenBank Accession No. Q1LZB6, Jun. 10, 2008.
GenBank Accession No. XM_853016, Aug. 30, 2005.

Patent Examination Report No. 1 issued Oct. 14, 2014, in Australian Patent Application No. 2009278387.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," J. Immunol. (2002), vol. 169, pp. 3076-3084.
Extended European Search Report issued Mar. 2, 2015, in European Patent Application No. 12819759.7.
Office Action issued Jan. 28, 2015, in Russian Patent Application No. 2012137502, with partial English translation.
Riechmann et al., "Reshaping human antibodies for therapy," Nature (Mar. 24, 1988), vol. 332, pp. 323-327.
Vajdos et al.,. "Comprehensive Functional Maps of the Antigen-binding Site of an Anti-ErbB2 Antibody Obtained with Shotgun Scanning Mutagenesis," J. Mol. Biol. (2002), vol. 320, pp. 415-428.
Buchsbaum et al., "Treatment of Pancreatic Cancer Xenografts with Erbitux (IMC-C225) Anti-EGFR Antibody, Gemcitabine, and Radiation," Int. J. Radiation Oncology Biol. Phys. (2002), vol. 54, No. 4, pp. 1180-1193.
Chames et al., "Therapeutic Antibodies for the Treatment of Pancreatic Cancer," The Scientific World Journal (Jan. 1, 2010), vol. 10, pp. 1107-1120.
Eccleston et al., "Pancreatic Tumor Marker Anti-Mucin Antibody CAM 17.1 Reacts with a Sialyl Blood Group Antigen, Probably I, Which is Expressed throughout the Human Gastrointestinal Tract," Digestion (1998), vol. 59, pp. 665-670.
Esteva et al., "Chemotheraphy of Metastatic Breast Cancer: What to Expect in 2001 and Beyond," The Oncologist (2001), vol. 6, pp. 133-146.
Extended European Search Report issued Feb. 2, 2015, in European Patent Application No. 12819473.5.
Extended European Search Report issued Jan. 29, 2015, in European Patent Application No. 12819899.1.
Houghton, P. J. and J. A. Houghton, "Evaluation of Single-Agent Therapy in Human Colorectal Tumour Xenografts," Br. J. Cancer (1978), vol. 37, pp. 833-840.
Gong et al., "Caprin-1 is a novel microRNA-223 target for regulating the proliferation and invasion of human breast cancer cells," Biomedicine & Pharmacotherapy (2013), vol. 67, pp. 629-636.
Qui et al., "Targeting a ribonucleoprotein complex containing the caprin-1 protein and the c-Myc mRNA suppresses tumor growth in mice: an identification of a novel oncotarget," Oncotarget (2014), vol. 6, No. 4, pp. 2148-2163.
Sabile et al., "Caprin-1, a novel Cyr61-interacting protein, promotes osteosarcoma tumor growth and lung metastasis in mice," Biochimica et Biophysica Acta (2013), vol. 1832, pp. 1173-1182.
Bodey et al., "MAGE-1, a Cancer/Testis-Antigen, Expression in Childhood Astrocytomas as an Indicator of Tumor Progression," in vivo (2002) vol. 16, pp. 583-588.
Comtesse et al., "Probing the human natural autoantibody repertoire using an immunoscreening approach," Clin. Exp. Immunol. (2000), vol. 121, pp. 430-436.
International Search Report issued Nov. 18, 2014, in PCT International Application No. PCT/JP2014/071094.
Jager et al., "Identification of a Tissue-specific Putative Transcription Factor in Breast Tissue by Serological Screening of a Breast Cancer Library," Cancer Research (Mar. 1, 2001), vol. 61, pp. 2055-2061.
Jungbluth et al., "Immunohistochemical Analysis of NY-ESO-1 Antigen Expression in Normal and Malignant Human Tissues," Int. J. Cancer (2001), vol. 92, pp. 856-860.
Kohler et al., "Tumor antigen analysis in neuroblastoma by serological interrogation of bioinformatic data," Cancer Science (Nov. 2010), vol. 101, No. 11, pp. 2316-2324.
Nakamura et al. "Gene Expression Profile of Metastatic Human Pancreatic Cancer Cells Depends on the Organ Microenvironment," Cancer Research (Jan. 1, 2007), vol. 67, No. 1, pp. 139-148.
Non-Final Office Action issued Nov. 6, 2014, in U.S. Appl. No. 13/576,950.
Pegram et al., "Rational Combinations of Trastuzumab with Chemotherapeutic Drugs Used in the Treatment of Breast Cancer," Journal of the National Cancer Institute (May 19, 2004), vol. 96, No. 10, pp. 739-749.

(56) References Cited

OTHER PUBLICATIONS

Punt et al., "Edrecolomab alone or in combination with fluorouracil and folinic acid in the adjuvant treatment of stage III colon cancer: a randomised study," Lancet (Aug. 31, 2002), vol. 360, No. 9334, pp. 671-677.
Akiyoshi, "Cancer Vaccine Therapy Using Peptides Derived from Tumor-Rejection Antigens," Jpn J Cancer Chemother., vol. 24, No. 5, Mar. 1997, pp. 511-519, with English Abstract (p. 519).
Balmana et al., "BRCA in breast cancer: ESMO Clinical Recommendations," Annals of Oncology, vol. 20, Supplemental 4, 2009, pp. iv19-iv20.
Bodey et al., "Failure of Cancer Vaccines: The Significant Limitations of this Approach to Immunotherapy," Anticancer Research, vol. 20, 2000, pp. 2665-2676.
Brand et al., "Prospect for Anti-HER2 Receptor Therapy in Breast Cancer," Anticancer Research, vol. 26, 2006, pp. 463-470.
Brass et al., "Translation initiation factor eIF-4gamma is encoded by an amplified gene and induces an immune response in squamous cell lung carcinoma," Human Molecular Genetics, Vol, 6, No. 1, 1997, pp. 33-39.
Chamberlain et al., "Innovations and strategies for the development of anticancer vaccines," Expert Opinion on Pharmacotherapy, vol. 1, No. 4, 2000, pp. 603-614.
Ellis, et al., "Identification and Characterization of A Novel Protein (p137) Which Transcytoses Bidirectionally in Caco-2 Cells", The Journal of Biological Chemistry, Sep. 1, 1995, vol. 270, No. 35, pp. 20717-20723.
European Search Report, dated Aug. 13, 2013, for European Application No. 11739882.6.
European Search Report, dated Aug. 26, 2011, for European Application No. No. 09805010.7.
European Search Report, dated Jan. 30, 2013, for European Application 09805009.9.
European Search Report, dated Nov. 6, 2013, for European Application No. 11739876.8.
Evans et al., "Vaccine therapy for cancer-fact or fiction?", Q J Med, vol. 92, 1999, pp. 299-307.
GeneCards, "Cell Cycle Associated Protein 1—Biological research products for CAPRIN 1," updated Mar. 19, 2013, 10 pages.
Grill et al., "Activation/Division of Lymphocytes Results in Increased Levels of Cytoplasmic Activation/Proliferation-Associated Protein-1: Prototype of a New Family of Proteins," The Journal of Immunology, vol. 172, 2004, pp. 2389-2400.
Güre et al., "Human Lung Cancer Antigens Recognized by Autologous Antibodies: Definition of a Novel cDNA Derived from the Tumor Suppressor Gene Locus on Chromosome 3p21.3," Cancer Research, vol. 58, Mar. 1, 1998, pp. 1034-1041.
Gure et al., "SSX: A Multigene Family with Several Members Transcribed in Normal Testis and Human Cancer," Int. J. Cancer, vol. 72, 1997, pp. 965-971.
Harlow et al., "Antibodies A Laboratory Manual", Cold Spring Harbor Laboratory, Chapter 3, 1988, pp. 23-34.
Hugo Gene Nomenclature Committee, Gene Symbol Report, CAPRIN1, Approved Name: Cell Cycle Associated Protein 1, HGNC ID: HGNC:6743, Nov. 3, 2012, 2 pages.
International Search Report and Written Opinion of the International Searching Authority, dated Mar. 1, 2011, for International Application No. PCT/JP2011/052413.
International Search Report, dated Mar. 15, 2011, for International Application No. PCT/JP2011/052384.
International Search Report, dated Mar. 8, 2011, for International Application No. PCT/JP2011/052403.
International Search Report, dated Mar. 8, 2011, for International Application No. PCT/JP2011/052414.
International Search Report, dated Oct. 6, 2009, for International Application No. PCT/JP2009/063882.
International Search Report, dated Sep. 8, 2009, for International Application No. PCT/JP2009/063883.
Itoh et al., "HUB1 is an autoantigen frequently eliciting humoral immune response in patients with adult T cell leukemia," Int. J. Oncol., vol. 14, No. 4, Apr. 1999, pp. 703-708 (Abstract only provided).
Jang et al., "Antihypertensive Angiotensin I-Converting Enzyme Inhibitory Activity and Antioxidant Activity of *Vitis hybrid-Vitis coignetiae* Red Wine Made with *Saccharomyces cerevisiae*," Mycobiology, vol. 39, No. 2, 2011, pp. 137-139.
Kaddar et al., "Two new miR-16 targets: caprin-1 and HMGA1, proteins implicated in cell proliferation," Biology of the Cell, vol. 101, No. 9, 2009, pp. 511-524.
Kajiji et al., "Six Monoclonal Antibodies to Human Pancreatic Cancer Antigens," Cancer Research, vol. 47, Mar. 1, 1987, pp. 1367-1376.
Karauzum et al., "Caprin 1 is Frequently Overexpressed in Human Lymphomas," American Society of Human Genetics, Cancer Genetics, Program No. 1190W, Oct. 12, 2011, One page (Abstract only).
Kataja et al., "Primary breast cancer: ESMO Clinical Recommendations for diagnosis, treatment and follow-up," Annals of Oncology, vol. 20, Supplement 4, 2009, pp. iv10-iv14.
Katsafanas et al., "Colocalization of Transcription and Translation within Cytoplasmic Poxvirus Factories Coordinates Viral Expression and Subjugates Host Functions," Cell Host & Microbe, vol. 2, Oct. 2007, pp. 221-228.
Katsafanas et al., "Vaccinia Virus Intermediate Stage Transcription Is Complemented by Ras-GTPase-activating Protein SH3 Domain-binding Protein (G3BP) . . .," Jour. of Biol. Chem., vol. 279, No. 50, Dec. 10, 2004, pp. 52210-52217.
Kolobova et al., "Microtubule-dependent association of AKAP350A and CCAR1 with RNA stress granules," Experimental Cell Research, vol. 315, 2009 (Available online Dec. 3, 2008), pp. 542-555.
Lu et al., "Identification of an immunological signature of tumor rejection in the neu transgenic mouse," 2007 AACR Annual Meeting, Apr. 14-18, 2007 (Presentation conducted on Apr. 17, 2007), One page (Abstract only provided).
Lu et al., "Targeting serum antibody for cancer diagnosis: a focus on colorectal cancer," Expert Opin. Ther. Targets, vol. 11, No. 2, 2007, pp. 235-244.
Müller-Pillasch et al., "Identification of a new tumour-associated antigen TM4SF5 and its expression in human cancer," Gene, vol. 208, 1998, pp. 25-30.
Munodzana et al., "Conformational Dependence of *Anaplasma marginale* Major Surface Protein 5 Surface-Exposed B-Cell Epitopes", Infection and Immunity, vol. 66, No. 6, Jun. 1998, pp. 2619-2624.
NCBI Reference Sequence, caprin-1 [*Bos taurus*], 2009, Accession No. NP_001069530, XP_615677, 1 page.
NCBI Reference Sequence, caprin-1 [*Gallus gallus*], 2005, Accession No. NP_001026536, XP_423820, 1 page.
NCBI Reference Sequence, caprin-1 isoform 1 [*Homo sapiens*], 1995, Accession No. NP_005889, 3 pages.
NCBI Reference Sequence, caprin-1 isoform 2 [*Homo sapiens*], 1995, Accession No. NP_976240, 3 pages.
NCBI Reference Sequence, caprin-1 isoform a [*Mus musculus*], 1996, Accession No. NP_058019, 3 pages.
NCBI Reference Sequence, caprin-1 isoform b [*Mus musculus*], 1996, Accession No. NP_001104760, 3 pages.
NCBI Reference Sequence, caprin-1 isoform c [*Mus musculus*], 1996, Accession No. NP_001104761, 4 pages.
NCBI Reference Sequence, Predicted: caprin-1 [*Equus caballus*], 2008, Accession No. XP_001492799, 1 page.
NCBI Reference Sequence, Predicted: caprin-1 isoform 2 [*Canis lupus familiaris*], Dec. 2, 2011, Accession No. XP_858109, 1 page.
Nelson et al., "Screening for Breast Cancer: An Update for the U.S. Preventive Services Task Force," Ann. Intern. Med., vol. 151, No. 10, Nov. 17, 2009, pp. 727-737.
Okano et al., "Abstract 519: Identification of a novel target for antibody therapy of breast cancer", Cancer Research, vol. 72, Issue 8, Supplement 1, Apr. 15, 2012, XP-002700046, 2 pages.
Polyak et al., "Alanine-170 and proline-172 are critical determinants for extracellular CD20 epitopes; heterogeneity in the fine specificity

(56) References Cited

OTHER PUBLICATIONS of CD20 monoclonal antibodies is defined by additional requirements imposed by both amino acid sequence . . .", Blood, vol. 99, No. 9, May 1, 2002, pp. 3256-3262.
R & D Systems, "IHC Products & Protocol Guide," printed Jan. 9, 2014, pp. 1-112.
Sahin et al., "Human neoplasms elicit multiple specific immune responses in the autologous host," Proc. Natl. Acad. Sci. USA, vol. 92, Dec. 1995, pp. 11810-11813.
Scanlan et al., "Cancer-related Serological Recognition of Human Colon Cancer: Identification of Potential Diagnostic and Immunotherapeutic Targets," Cancer Research, vol. 62, Jul. 15, 2002, pp. 4041-4047.
Scanlan et al., "Characterization of Human Colon Cancer Antigens Recognized by Autologous Antibodies," Int. J. Cancer, vol. 76, 1998, pp. 652-658.
Solomon et al., "Distinct Structural Features of Caprin-1 Mediate Its Interaction with G3BP-1 and Its Induction of Phosphorylation of Eukaryotic Translation Initiation Factor 2α, Entry to Cytoplasmic Stress . . .," Molecular and Cellular Biology, vol. 27; No. 6, Mar. 2007, XP_002690351, pp. 2324-2342.
Strome et al., "A Mechanistic Perspective of Monoclonal Antibodies in Cancer Therapy Beyond Target-Related Effects," The Oncologist, vol. 12, 2007, pp. 1084-1095.
Türeci et al., "The SSX-2 Gene, Which Is Involved in the t(X; 18) Translocation of Synovial Sarcomas, Codes for the Human Tumor Antigen HOM-MEL-40," Cancer Research, vol. 56, Oct. 15, 1996, pp. 4766-4772.
United States Notice of Allowance, dated Dec. 2, 2013, for U.S. Appl. No. 13/576,955.
United States Office Action, dated Aug. 19, 2013, for U.S. Appl. No. 13/576,955.
United States Office Action, dated Aug. 26, 2013, for U.S. Appl. No. 13/576,950.
United States Office Action, dated Dec. 21, 2012, for U.S. Appl. No. 13/057,515.
United States Office Action, dated Dec. 21, 2012, for U.S. Appl. No. 13/057,709.
United States Office Action, dated Jan. 16, 2014, for U.S. Appl. No. 13/057,515.
United States Office Action, dated Jul. 1, 2013, for U.S. Appl. No. 13/057,515.
United States Office Action, dated Jul. 1, 2013, for U.S. Appl. No. 13/577,212.
United States Office Action, dated Jul. 16, 2013, for U.S. Appl. No. 13/057,709.
United States Office Action, dated Jun. 14, 2013, for U.S. Appl. No. 13/576,969.
United States Office Action, dated Mar. 13, 2013, for U.S. Appl. No. 13/576,955.
United States Office Action, dated Nov. 15, 2013, for U.S. Appl. No. 13/576,953.
United States Office Action, dated Nov. 15, 2013, for U.S. Appl. No. 13/577,028.
United States Office Action, dated Nov. 15, 2013, in U.S. Appl. No. 13/576,950.
United States Office Action, dated Nov. 2, 2012, for U.S. Appl. No. 13/057,709.
United States Office Action, dated Nov. 9, 2012, for U.S. Appl. No. 13/057,515.
United States Office Action, dated Oct. 15, 2013, for U.S. Appl. No. 13/576,969.
United States Office Action, dated Oct. 21, 2013, for U.S. Appl. No. 13/577,212.
United States Office Action, dated Sep. 19, 2013, for U.S. Appl. No. 13/577,028.
United States Office Action, dated Sep. 6, 2013, for U.S. Appl. No. 13/576,953.
Van Der Bruggen et al., "A Gene Encoding an Antigen Recognized by Cytolytic T Lymphocytes on a Human Melanoma," Science, vol. 254, Dec. 13, 1991, pp. 1643-1647 (Also published in J. Immunol., vol. 178, 2007, pp. 2617-2621).
Wang et al., "Absence of Caprin-1 Results in Defects in Cellular Proliferation", The Journal of Immunology, 2005, vol. 175, pp. 4274-4282.
Yanai et al., "Dlk-1, a cell surface antigen on foetal hepatic stem/progenitor cells, is expressed in hepatocellular, colon, pancreas and breast carcinomas at a high frequency," The Journal of Biochemistry, vol. 148, No. 1, 2010 (Publ. online Mar. 30, 2010), pp. 85-92.
Extended European Search Report issued Mar. 18, 2015, in European Patent Application No. 12820225.6.
Extended European Search Report issued Mar. 23, 2015, in European Patent Application No. 12820596.0.
Non-Final Office Action issued Apr. 14, 2015, in U.S. Appl. No. 14/236,793.
GenBank Accession No. NM_005898, Feb. 11, 2008.

PHARMACEUTICAL COMPOSITION FOR TREATMENT AND/OR PROPHYLAXIS OF CANCER

TECHNICAL FIELD

The present invention relates to novel use of an antibody against CAPRIN-1 or a fragment thereof in a drug such as a therapeutic and/or preventive agent for cancer.

BACKGROUND ART

Cancer is the leading cause of death. This disease is currently treated principally by surgical therapy in combination with radiation therapy and/or chemotherapy. In spite of recent development of novel surgical techniques or discovery of novel anticancer agents, the existing treatment of cancer has an insufficiently improved outcome, except for some cancer types. With recent advances of molecular biology or cancer immunology, antibodies that specifically react with cancer, cancer antigens that are recognized by cytotoxic T cells, genes encoding such cancer antigens, and the like have been identified, raising expectations on specific cancer therapy targeting the cancer antigens (Non Patent Literature 1).

For reducing the side effect of cancer therapy, it is desired that peptides, polypeptides, or proteins recognized as antigens of the cancer should rarely exist in normal cells and specifically exist in cancer cells. In 1991, Boon et al. (Ludwig Institute for Cancer Research, Belgium) isolated a human melanoma antigen MAGE1 recognized by CD8-positive T cells by a cDNA expression cloning method using autologous cancer cell lines and cancer-reactive T cells (Non Patent Literature 2). Then, a SEREX (serological identification of antigens by recombinant expression cloning) method has been reported, which adopts a gene expression cloning approach to identify tumor antigens recognized by antibodies produced in response to autologous cancer in vivo in a cancer patient (Non Patent Literature 3 and Patent Literature 1). According to this method, some cancer antigens that are rarely expressed in normal cells and are specifically expressed in cancer have been isolated (Non Patent Literatures 4 to 9). In addition, cell therapy using immunocytes that specifically react with cancer antigens or cancer-specific immunotherapy using vaccines or the like comprising cancer antigens is under clinical trial targeting some of the isolated cancer antigens.

In recent years, various antibody drugs for cancer treatment targeting antigenic proteins on cancer cells have emerged in the world. These drugs have received attention because of their certain efficacy as cancer-specific therapeutic agents. A large majority of antigenic proteins targeted by the drugs, however, are also expressed in normal cells. As a result of administering the antibodies, normal cells expressing the antigens as well as cancer cells are damaged, disadvantageously resulting in side effect. Thus, if cancer antigens specifically expressed on the surface of cancer cells can be identified and antibodies targeting the antigens can be used as drugs, these antibody drugs can be expected to achieve treatment with less side effect.

Cytoplasmic-activation- and proliferation-associated protein 1 (CAPRIN-1) has been known as an intracellular protein that is expressed upon activation or cell division of resting normal cells and forms cytoplasmic stress granules with intracellular RNAs to participate in the regulation of transport and translation of mRNAs. This protein has been found to be specifically expressed on the surface of cancer cells and is therefore under study as a target of antibody drugs for cancer treatment (Patent Literature 2).

CITATION LIST

Patent Literature

Patent Literature 1: U.S. Pat. No. 5,698,396
Patent Literature 2: WO2010/016526

Non Patent Literature

Non Patent Literature 1: Tsuyoshi Akiyoshi, "Japanese Journal of Cancer and Chemotherapy", 1997, Vol. 24, p. 511-519 (Japanese Journal of Cancer and Chemotherapy Publishers Inc., Japan)
Non Patent Literature 2: Bruggen P. et al., Science, 254: 1643-1647 (1991)
Non Patent Literature 3: Proc. Natl. Acad. Sci. USA, 92: 11810-11813 (1995)
Non Patent Literature 4: Int. J. Cancer, 72: 965-971 (1997)
Non Patent Literature 5: Cancer Res., 58: 1034-1041 (1998)
Non Patent Literature 6: Int. J. Cancer, 29: 652-658 (1998)
Non Patent Literature 7: Int. J. Oncol., 14: 703-708 (1999)
Non Patent Literature 8: Cancer Res., 56: 4766-4772 (1996)
Non Patent Literature 9: Hum. Mol. Genet. 6: 33-39, 1997

SUMMARY OF INVENTION

Technical Problem

An object of the present invention is to produce an antibody which targets CAPRIN-1 specifically expressed on the surface of cancer cells and has better antitumor activity than conventional antibodies, and provide use of the antibody as a therapeutic and/or preventive agent for cancer.

Solution to Problem

The present invention has the following aspects:

The present invention provides an antibody or a fragment thereof which has immunological reactivity with a CAPRIN-1 protein, the antibody or the fragment thereof comprising a heavy chain variable region comprising amino acid sequences represented by SEQ ID NOs: 5, 6, and 7 and a light chain variable region comprising amino acid sequences represented by SEQ ID NOs: 9, 10, and 11.

In another embodiment, the antibody is a human antibody, a humanized antibody, a chimeric antibody, a single-chain antibody, or a bispecific antibody.

The present invention provides a pharmaceutical composition for treatment and/or prevention of cancer, comprising the antibody or the fragment thereof as an active ingredient.

In an embodiment of the present invention, the cancer is breast cancer, kidney cancer, pancreatic cancer, large bowel cancer, lung cancer, brain tumor, gastric cancer, uterine cervix cancer, ovary cancer, prostate cancer, urinary bladder cancer, esophageal cancer, leukemia, lymphoma, fibrosarcoma, mastocytoma, or melanoma.

The present specification encompasses the contents disclosed in Japanese Patent Application No. 2011-171379 based on which the priority of the present application is claimed.

Advantageous Effects of Invention

The antibody against CAPRIN-1 used in the present invention damages cancer cells. Thus, the antibody against CAPRIN-1 is useful in the treatment and/or prevention of cancer.

DESCRIPTION OF EMBODIMENTS

The antibody against a CAPRIN-1 polypeptide used in the present invention can be examined for its antitumor activity, as described later, by examining in vivo the inhibition of tumor proliferation in a cancer-bearing animal or by examining ex vivo the presence or absence of immunocyte- or complement-mediated cytotoxic activity exhibited by the antibody against tumor cells expressing the polypeptide.

The antibody against CAPRIN-1 used in the present invention is a monoclonal antibody specifically binding to the CAPRIN-1 protein. Such a monoclonal antibody may be any type of antibody that can exert antitumor activity and includes, for example, non-human animal antibodies (e.g., mouse, rat, rabbit, and chicken monoclonal antibodies), recombinant antibodies (e.g., synthetic antibodies, multispecific antibodies, humanized antibodies, chimeric antibodies, and single-chain antibodies (scFv)), human antibodies, and their antibody fragments (e.g., Fab, F(ab')$_2$, and Fv). These antibodies and fragments thereof can be prepared by methods generally known to those skilled in the art. In the case of a human test subject, a human antibody or a humanized antibody is desirable for avoiding or suppressing rejection.

The antibody is any class of immunoglobulin molecule, for example, IgG, IgE, IgM, IgA, IgD, or IgY, or any subclass, for example, IgG1, IgG2, IgG3, IgG4, IgA1, or IgA2.

The antibody may be further modified by acetylation, formylation, amidation, phosphorylation, PEGylation, or the like, in addition to glycosylation.

In this context, the phrase "specifically binding to the CAPRIN-1 protein" means that the antibody specifically binds to the CAPRIN-1 protein without substantially binding to other proteins.

The test subject to receive the treatment and/or prevention of cancer according to the present invention is a mammal such as a human, a pet animal, livestock, or a sport animal, preferably a human.

Hereinafter, antigen preparation, antibody preparation, and a pharmaceutical composition according to the present invention will be described.

<Preparation of Antigen for Antibody Preparation>

Proteins or fragments thereof used as sensitizing antigens for obtaining the antibody against CAPRIN-1 used in the present invention are not limited by animal types serving as their origins, including humans, dogs, cattle, horses, mice, rats, and chickens. The proteins or the fragments thereof, however, are preferably selected in view of compatibility with parent cells for use in cell fusion. In general, mammal-derived proteins are preferred. Particularly, human-derived proteins are preferred. For example, when CAPRIN-1 is human CAPRIN-1, human CAPRIN-1 proteins, partial peptides thereof, or cells expressing human CAPRIN-1 can be used as sensitizing antigens.

The nucleotide sequences and amino acid sequences of human CAPRIN-1 and homologs thereof can be obtained, for example, by making an access to GenBank (NCBI, USA) and using BLAST or FASTA algorithm (Karlin and Altschul, Proc. Natl. Acad. Sci. USA, 90: 5873-5877, 1993; and Altschul et al., Nucleic Acids Res. 25: 3389-3402, 1997).

In the present invention, with reference to the nucleotide sequence (SEQ ID NO: 1 or 3) or amino acid sequence (SEQ ID NO: 2 or 4) of human CAPRIN-1, the targets are nucleic acids or proteins consisting of sequences having 70% to 100%, preferably 80% to 100%, more preferably 90% to 100%, further preferably 95% to 100%, for example, 97% to 100%, 98% to 100%, 99% to 100%, or 99.5% to 100% sequence identity to the nucleotide sequence or amino acid sequence of the ORF or mature portion of the reference. In this context, the term "% sequence identity" means a percentage (%) of the number of identical amino acids (or bases) to the total number of amino acids (or bases) when two sequences are aligned such that the maximum degree of similarity or identity can be achieved with or without introduced gaps.

The fragments of each CAPRIN-1 protein have lengths ranging from the amino acid length of an epitope (or an antigenic determinant), which is the smallest unit recognized by the antibody, to less than the full-length of the protein. The epitope refers to a polypeptide fragment having antigenicity or immunogenicity in mammals, preferably humans. Its smallest unit consists of approximately 7 to 12 amino acid, for example, 8 to 11 amino acid.

Polypeptides comprising the above human CAPRIN-1 proteins and partial peptides thereof can be synthesized according to chemical synthesis methods, for example, Fmoc (fluorenylmethyloxycarbonyl) and tBoc (t-butyloxycarbonyl) methods (Seikagaku Jikken Koza (Biochemical Experimentation Course in English) 1, the Japanese Biochemical Society ed., Protein Chemistry IV, Chemical Modification and Peptide Synthesis, Tokyo Kagaku Dojin Co., Ltd. (Japan), 1981). Also, these polypeptides can be synthesized by routine methods using various commercially available peptide synthesizers. Alternatively, polynucleotides encoding the polypeptides may be prepared using genetic engineering approaches known in the art (Sambrook et al., Molecular Cloning, the 2nd edition, Current Protocols in Molecular Biology (1989), Cold Spring Harbor Laboratory Press; Ausubel et al., Short Protocols in Molecular Biology, the 3rd edition, A compendium of Methods from Current Protocols in Molecular Biology (1995), John Wiley & Sons; etc.) and incorporated into expression vectors, which are then introduced into host cells so that the host cells produce the polypeptides. In this way, the polypeptides of interest can be obtained.

The polynucleotides encoding the polypeptides can be readily prepared by genetic engineering approaches known in the art or routine methods using commercially available nucleic acid synthesizers. For example, a DNA comprising the nucleotide sequence of human CAPRIN-1 gene can be prepared by PCR using a human chromosomal DNA or cDNA library as a template and a pair of primers designed so as to be capable of amplifying the nucleotide sequence described in SEQ ID NO: 1. Reaction conditions for this PCR can be appropriately determined. Examples of the conditions can include, but not limited to, 30 cycles each involving reaction steps consisting of 94° C. for 30 seconds (denaturation), 55° C. for 30 seconds to 1 minute (annealing), and 72° C. for 2 minutes (elongation) using thermotolerance DNA polymerase (e.g., Taq polymerase, Pfu polymerase) and a $Mg^{2+}$-containing PCR buffer, followed by reaction at 72° C. for 7 minutes. The PCR approach, conditions, etc. are described in, for example, Ausubel et al., Short Protocols in Molecular Biology, the 3rd edition, A Compendium of Methods from Current Protocols in Molecular Biology (1995), John Wiley & Sons (particularly, Chapter 15).

Also, appropriate probes or primers can be prepared on the basis of information about the nucleotide sequences of CAPRIN-1 gene and the amino acid sequences of CAPRIN-1 proteins, and used in the screening of, for example, a human cDNA library, to isolate the desired DNA. Preferably, such a cDNA library is produced from cells, organs, or tissues expressing CAPRIN-1 proteins. Examples of such cells or tissues include cells or tissues derived from the testis or from cancers or tumors such as leukemia, breast cancer, lymphoma, brain tumor, lung cancer, pancreatic cancer, and large bowel cancer. These operations, including the preparation of probes or primers, the construction of a cDNA library, the screening of the cDNA library, and the cloning of the gene of interest, are known to those skilled in the art and can be performed according to methods described in, for example, Sambrook et al., Molecular Cloning, the 2nd edition, Current Protocols in Molecular Biology (1989), and Ausubel et al. (ibid.). DNAs encoding the human CAPRIN-1 proteins and the partial peptides thereof can be obtained from the DNA thus obtained.

The host cells may be any cell capable of expressing the above polypeptides. Examples of prokaryotic cells include, but not limited to, *E. coli*. Examples of eukaryotic cells include, but not limited to: mammalian cells such as monkey kidney cells COS1 and Chinese hamster ovary cells CHO; a human embryonic kidney cell line HEK293; mouse embryonic skin cell line NIH3T3; yeast cells such as budding yeast and fission yeast cells; silkworm cells; and *Xenopus* egg cells.

In the case of using prokaryotic cells as the host cells, the expression vectors used have an origin that permits replication in the prokaryotic cells, a promoter, a ribosomal binding site, a multicloning site, a terminator, a drug resistance gene, an auxotrophic complementary gene, etc. Examples of expression vectors for *E. coli* can include pUC series, pBluescript II, pET expression systems, and pGEX expression systems. The DNAs encoding the above polypeptides can be incorporated into such expression vectors, with which prokaryotic host cells are then transformed, followed by culture of the obtained transformants so that the polypeptides encoded by the DNAs are expressed in the prokaryotic host cells. In this respect, the polypeptides may be expressed as fusion proteins with other proteins.

In the case of using eukaryotic cells as the host cells, expression vectors for eukaryotic cells having a promoter, a splicing region, a poly(A) addition site, etc. are used as the expression vectors. Examples of such expression vectors can include pKA1, pCDM8, pSVK3, pMSG, pSVL, pBK-CMV, pBK-RSV, EBV, pRS, pcDNA3, and pYES2 vectors. In the same way as above, the DNAs encoding the above polypeptides can be incorporated into such expression vectors, with which eukaryotic host cells are then transformed, followed by culture of the obtained transformants so that the polypeptides encoded by the DNAs are expressed in the eukaryotic host cells. In the case of using expression vectors such as pIND/V5-His, pFLAG-CMV-2, pEGFP-N1, or pEGFP-C1, the polypeptides may be expressed as various fusion proteins tagged with His tag (e.g., (His)$_6$-(His)$_{10}$), FLAG tag, myc tag, HA tag, GFP, or the like.

The expression vectors can be introduced into the host cells using well known methods such as electroporation, a calcium phosphate method, a liposome method, a DEAE dextran method, microinjection, viral infection, lipofection, and binding with cell-penetrating peptides.

The polypeptide of interest can be isolated and purified from the host cells by a combination of separation operations known in the art. Examples thereof include, but not limited to, treatment with a denaturant (e.g., urea) or a detergent, ultrasonication, enzymatic digestion, salting-out, solvent fractionation and precipitation, dialysis, centrifugation, ultrafiltration, gel filtration, SDS-PAGE, isoelectric focusing electrophoresis, ion-exchange chromatography, hydrophobic chromatography, affinity chromatography, and reverse-phase chromatography.

<Structure of Antibody>

Antibodies are usually heteromultimeric glycoproteins comprising at least two heavy chains and two light chains. The immunoglobulins other than IgM are heterotetrameric glycoproteins of approximately 150 kDa each composed of two identical light (L) chains and two identical heavy (H) chains. Typically, each light chain is connected to a heavy chain via a single covalent disulfide bond, though the number of disulfide bonds between heavy chains varies among different immunoglobulin isotypes. Each of the heavy and light chains also has an intrachain disulfide bond. Each heavy chain has a variable domain (VH region) at one end, followed by a series of constant regions. Each light chain has a variable domain (VL region) at one end and has a single constant region at the other end. The light chain constant region is aligned with the first heavy chain constant region, while the light chain variable domain is aligned with the heavy chain variable domain. Particular regions called complementarity determining regions (CDRs) in the antibody variable domains exhibit specific variability and impart binding specificity to the antibody. Portions relatively conserved in the variable regions are called framework regions (FRs). The complete heavy and light chain variable domains each comprise four FRs connected via three CDRs. These three CDRs are called CDRH1, CDRH2, and CDRH3 in this order from the N-terminus of the heavy chain. Likewise, the CDRs are called CDRL1, CDRL2, and CDRL3 in the light chain. CDRH3 is most important for the binding specificity of the antibody for its antigen. In addition, CDRs in each chain are kept close to each other by the FR regions and contribute to the formation of an antigen-binding site in the antibody, together with CDRs in the other chain. The constant regions do not directly contribute to antibody-antigen binding, but exhibit various effector functions, for example, involvement in antibody-dependent cellular cytotoxicity (ADCC), phagocytosis mediated by binding to an Fcγ receptor, half-life/clearance rate mediated by a neonatal Fc receptor (FcRn), and complement-dependent cytotoxicity (CDC) mediated by a C1q component in the complement cascade.

<Preparation of Antibody>

The anti-CAPRIN-1 antibody according to the present invention means an antibody having immunological reactivity with a full-length CAPRIN-1 protein or a fragment thereof.

In this context, the "immunological reactivity" means the property of the antibody binding to the CAPRIN-1 antigen in vivo. Via such binding, the antibody exerts the function of damaging (e.g., killing, suppressing, or regressing) tumor. Specifically, the antibody used in the present invention is not limited by its type as long as the antibody can damage tumors such as breast cancer, kidney cancer, pancreatic cancer, large bowel cancer, lung cancer, brain tumor, gastric cancer, uterine cervix cancer, ovary cancer, prostate cancer, urinary bladder cancer, esophageal cancer, leukemia, lymphoma, fibrosarcoma, mastocytoma, or melanoma as a result of binding to the CAPRIN-1 protein.

Hereinafter, preparation examples of various monoclonal antibodies will be shown.

For example, breast cancer cell lines SK-BR-3 expressing CAPRIN-1 is administered to each mouse for immunization. The spleen is extracted from this mouse. After separation of spleen cells, the cells are fused with mouse myeloma cells. Clones producing antibodies having antiproliferative effect a cancer cell are selected from among the obtained fusion cells (hybridomas). The hybridomas producing monoclonal antibodies having antiproliferative effect of a cancer cell are isolated and cultured. The antibody can be prepared by purification from the culture supernatant according to a general affinity purification method.

The monoclonal antibody-producing hybridomas may be prepared, for example, as follows: first, animals are immunized with sensitizing antigens according to a method known in the art. This immunization method generally involves intraperitoneally or subcutaneously injecting the sensitizing antigens to mammals. Specifically, the sensitizing antigens are diluted with or suspended in PBS (phosphate-buffered saline), physiological saline, or the like into an appropriate amount and then mixed, if desired, with an appropriate amount of a conventional adjuvant, for example, a complete Freund's adjuvant. After emulsification, the resulting emulsion is administered to each mammal several times every 4 to 21 days. Alternatively, an appropriate carrier may be used for the immunization with sensitizing antigens.

After confirmation of a rise in the level of the desired antibody in the serum of the mammal thus immunized, immunocytes are collected from the mammal and subjected to cell fusion. Preferred examples of the immunocytes particularly include spleen cells.

Mammalian myeloma cells are used as partner parent cells to be fused with the immunocytes. For the myeloma cells, various cell lines known in the art, for example, P3U1 (P3-X63Ag8U1), P3 (P3x63Ag8.653) (J. Immunol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (deSt. Groth, S. F. et al., J. Immunol. Methods (1980) 35, 1-21), S194 (Trowbridge, I. S. J. Exp. Med. (1978) 148, 313-323), and 8210 (Galfre, G. et al., Nature (1979) 277, 131-133), are preferably used.

The cell fusion between the immunocytes and the myeloma cells can be performed basically according to a method known in the art, for example, the method of Kohler and Milstein (Kohler, G. and Milstein, C. Methods Enzymol. (1981) 73, 3-46).

More specifically, the cell fusion is carried out, for example, in the presence of a cell fusion promoter in a conventional nutrient medium. For example, polyethylene glycol (PEG) or hemagglutinating virus of Japan (HVJ) is used as the fusion promoter. If desired, an auxiliary such as dimethyl sulfoxide may be further added in order to enhance fusion efficiency.

The ratio between the immunocytes and the myeloma cells used can be arbitrarily set. For example, the amount of the immunocytes is preferably set to 1 to 10 times the amount of the myeloma cells. Examples of the medium that can be used in the cell fusion include RPMI1640 and MEM media suitable for the growth of the myeloma cell lines as well as conventional media for use in this type of cell culture. In addition, a serum supplement such as fetal calf serum (FCS) may be used in combination with these media.

For the cell fusion, the immunocytes and the myeloma cells are well mixed in a predetermined amount of the medium. A PEG solution (average molecular weight: for example, approximately 1000 to 6000) preheated to approximately 37° C. is usually added to the mixture at a concentration of 30 to 60% (w/v) and mixed therewith to form the hybridomas of interest. Subsequently, procedures of sequentially adding an appropriate medium and removing the supernatant by centrifugation are repeated to remove cell fusion agents or the like unfavorable for the growth of the hybridomas.

The hybridomas thus obtained are cultured in a conventional selective medium, for example, a HAT medium (medium containing hypoxanthine, aminopterin, and thymidine) for selection. Culture in the HAT medium is continued for a period (usually, several days to several weeks) sufficient for the death of cells other than the hybridomas of interest (non-fused cells). Subsequently, hybridomas producing the antibody of interest are screened for and cloned as single clones by a conventional limiting dilution method.

In addition to such obtainment of the hybridomas by the immunization of non-human animals with antigens, hybridomas producing human antibodies having the desired activity (e.g., cell antiproliferative activity) may be obtained by sensitizing human lymphocytes, for example, EB virus-infected human lymphocytes, with proteins, protein-expressing cells, or lysates thereof in vitro and fusing the sensitized lymphocytes with human-derived myeloma cells capable of dividing permanently, for example, U266 (Accession No. TIB 196).

The monoclonal antibody-producing hybridomas thus prepared can be subcultured in a conventional medium and can also be stored for a long period in liquid nitrogen.

Specifically, the desired antigens or cells expressing the desired antigens are used as sensitizing antigens in immunization according to a conventional immunization method. The obtained immunocytes are fused with parent cells known in the art according to a conventional cell fusion method. Monoclonal antibody-producing cells (hybridomas) can be screened for by a conventional screening method to prepare the antibody.

In this context, for example, KM mice (Kirin Pharma Co., Ltd./Medarex) and Xeno mice (Amgen Inc.) are known as the human antibody-producing mice (e.g., International Publication Nos. WO02/43478 and WO02/092812). Complete human polyclonal antibodies can be obtained from the blood of such mice immunized with CAPRIN-1 proteins or fragments thereof. Alternatively, spleen cells may be isolated from the mice thus immunized and fused with myeloma cells. In this way, human monoclonal antibodies can be obtained.

The antigens can be prepared according to, for example, a method using animal cells (JP Patent Publication (Kohyo) No. 2007-530068) or a method using baculovirus (e.g., International Publication No. WO98/46777). Antigens having low immunogenicity can be bound to immunogenic macromolecules such as albumin for immunization.

Alternatively, recombinant antibodies may be used, which are produced using a gene recombination technique which involves: cloning the antibody genes from hybridomas; incorporating the antibody genes into appropriate vectors; and introducing the vectors into hosts (see, e.g., Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, cDNAs of the antibody variable region (V region) are synthesized from the mRNAs of hybridomas using reverse transcriptase. After obtainment of DNAs encoding the antibody V regions of interest, the DNAs are ligated with DNAs encoding the desired antibody constant regions (C regions). The resulting ligation products are then incorporated into expression vectors. Alternatively, the antibody V region-encoding DNAs may be incorporated into expression vectors containing antibody C region DNAs. These DNAs are incorporated into the expression vectors so as to be expressed under the control of expression control regions, for example, an enhancer and a promoter. Next, host cells can be transformed with the resulting expression vectors and allowed to express antibodies.

As described above, the anti-CAPRIN-1 antibody of the present invention is any of various monoclonal antibodies including non-human animal monoclonal antibodies, human monoclonal antibodies, and recombinant antibodies.

These non-human animal monoclonal antibodies or human monoclonal antibodies may be prepared by the culture of hybridomas obtained by the fusion between spleen cells from non-human animals (e.g., mice, human antibody-producing mice, chicken, or rabbits) immunized with CAPRIN-1 proteins and myeloma cells.

The recombinant antibody includes, as described above, chimeric antibodies, humanized antibodies, single-chain antibodies, multispecific antibodies, and the like.

The chimeric antibody can be prepared by: ligating DNAs encoding light or heavy chain variable regions of an antibody derived from a non-human animal (e.g., mouse, rat, rabbit, or chicken) with DNAs encoding light or heavy chain constant regions derived from a human antibody; incorporating the resulting fusion genes into expression vectors; and introducing the vectors into hosts so that antibodies are produced.

Specifically, the chimeric antibody is, for example, an antibody composed of variable regions of mouse antibody heavy and light chains and heavy and light chain constant region of human antibodies. The chimeric antibody can be prepared using a method known in the art which involves, for example: ligating DNAs encoding mouse antibody V regions with DNAs encoding human antibody C regions; incorporating the resulting ligation products into expression vectors; and introducing the vectors into hosts so that antibodies are produced. In Examples described later, human-mouse chimeric antibodies were prepared and confirmed to have an antitumor effect. These monoclonal antibodies comprise a heavy chain variable (VH) region having the amino acid sequence of SEQ ID NO: 8 and a light chain variable (VL) region having the amino acid sequence of SEQ ID NO: 12, wherein the VH region comprises CDR1 represented by the amino acid sequence of SEQ ID NO: 5, CDR2 represented by the amino acid sequence of SEQ ID NO: 6, and CDR3 represented by the amino acid sequence of SEQ ID NO: 7, and the VL region comprises CDR1 represented by the amino acid sequence of SEQ ID NO: 9, CDR2 represented by the amino acid sequence of SEQ ID NO: 10, and CDR3 represented by the amino acid sequence of SEQ ID NO: 11.

The humanized antibody, also called reshaped human antibody, is an engineered antibody. The humanized antibody is constructed by grafting CDRs of human antibody with CDRs corresponding to antibody derived from an immunized animal. Specifically, DNAs in which the CDR coding sequences in DNAs encoding a human antibody-derived light or heavy chain variable region are substituted by corresponding CDR coding sequences of a non-human animal (e.g., mouse, rat, rabbit, or chicken)-derived antibody are prepared and ligated with the DNAs encoding human antibody-derived light or heavy chain constant regions. The resulting fusion genes can be incorporated into expression vectors, which are then introduced into hosts for antibody production to prepare the humanized antibody of interest.

Specifically, for example, DNA sequences designed so as to link mouse and chicken antibodies CDRs and human antibody framework regions (FRs) are synthesized by PCR using several prepared oligonucleotides having terminal portions overlapping with each other. The obtained DNAs are ligated with DNAs encoding human antibody constant regions. Subsequently, the resulting ligation products are incorporated into expression vectors, which are then introduced into hosts for antibody production to obtain the antibody of interest (see European Patent Application Publication No. EP239400 and International Publication No. WO96/02576). The human antibody FRs connected via CDRs are selected such that the CDRs form a favorable antigen-binding site. If necessary, amino acids in the framework regions of antibody variable regions may be substituted so that the CDRs of the resulting reshaped human antibody form an appropriate antigen-binding site (Sato K. et al., Cancer Research 1993, 53: 851-856). In addition, these framework regions may be replaced with framework regions derived from various human antibodies (see International Publication No. WO99/51743).

The human antibody framework regions connected via CDRs are selected such that the CDRs form a favorable antigen-binding site. If necessary, amino acids in the framework regions of antibody variable regions may be substituted such that the CDRs of the resulting reshaped human antibody form an appropriate antigen-binding site (Sato K. et al., Cancer Research 1993, 53: 851-856).

The single-chain antibody refers to an antibody or the fragment thereof comprising variable regions of heavy and light chains linearly linked to each other via a linker. A DNA encoding the single-chain antibody can be prepared by ligating a DNA encoding the heavy chain variable region, a DNA encoding the linker, and a DNA encoding the light chain variable region. In this context, the variable regions of heavy and light chains are both derived from a human antibody or derived from a human antibody having CDRs alone substituted by CDRs of a non-human animal (e.g., mouse, rat, rabbit, or chicken)-derived antibody. The linker consists of 12 to 19 amino acids. Examples thereof include $(G_4S)_3$ consisting of 15 amino acids (G. B. Kim et al., Protein Engineering Design and Selection 2007, 20 (9): 425-432).

The multispecific antibody refers to an antibody capable of specifically binding a plurality of different epitopes. For example, the bispecific antibody (diabody) is capable of specifically binding to two different epitopes. A DNA encoding the bispecific antibody can be prepared by ligating, for example, a DNA encoding a heavy chain variable region A, a DNA encoding a light chain variable region B, a DNA encoding a heavy chain variable region B, and a DNA encoding a light chain variable region A in this order (provided that the DNA encoding a light chain variable region B and the DNA encoding a heavy chain variable region B are ligated via a DNA encoding a linker as described above). In this context, the variable regions of heavy and light chains are all derived from a human antibody or derived from a human antibody having CDRs alone substituted by CDRs of a non-human animal (e.g., mouse, rat, rabbit, or chicken)-derived antibody.

Amino acids in variable regions (e.g., FRs) or constant regions of the chimeric antibody or the humanized antibody thus prepared may be substituted by other amino acids.

The amino acid substitution is the substitution of, for example, less than 15, less than 10, 8 or less, 7 or less, 6 or less, 5 or less, 4 or less, 3 or less, or 2 or less amino acids, preferably 1 to 5 amino acids, more preferably 1 or 2 amino acids. The substituted antibody should be functionally equivalent to an unsubstituted antibody. The substitution is desirably conservative amino acid substitution, which is the substitution between amino acids similar in properties such as charge, side chains, polarity, and aromaticity. The amino acids can be classified in terms of similar properties into, for example: basic amino acids (arginine, lysine, and histidine); acidic amino acids (aspartic acid and glutamic acid); uncharged polar amino acids (glycine, asparagine, glutamine, serine, threonine, cysteine, and tyrosine); nonpolar amino acids (leucine, isoleucine, alanine, valine, proline, phenylalanine, tryptophan, and methionine); branched amino acids (leucine, valine, and isoleucine); and aromatic amino acids (phenylalanine, tyrosine, tryptophan, and histidine).

Examples of modified antibodies can include antibodies bound with various molecules such as polyethylene glycol (PEG). In the modified antibody of the present invention, the substance to be bound is not limited. In order to obtain such a modified antibody, the obtained antibody can be chemically modified. A method therefor has already been established in the art.

In this context, the phrase "functionally equivalent" means that an antibody concerned has biological or biochemical activity similar to that of the antibody of the present invention, specifically, the antibody concerned has the function of damaging tumor and essentially causes no rejection when applied to humans, for example. Examples of such activity can include antiproliferative activity and binding activity.

A method for preparing a polypeptide functionally equivalent to a certain polypeptide, which involves introducing a mutation into a polypeptide, is well known to those skilled in the art. For example, those skilled in the art can appropriately introduce a mutation into the antibody of the present invention using site-directed mutagenesis (Hashimoto-Gotoh, T. et al., (1995) Gene 152: 271-275; Zoller, M J., and Smith, M. (1983) Methods Enzymol., 100: 468-500; Kramer, W. et al., (1984) Nucleic Acids Res., 12: 9441-9456; Kramer, W. and Fritz, H J., (1987) Methods Enzymol., 154: 350-367; Kunkel, T A., (1985) Proc. Natl. Acad. Sci. USA., 82: 488-492; and Kunkel (1988) Methods Enzymol., 85: 2763-2766) or the like, thereby prepare an antibody functionally equivalent to the antibody of the present invention.

An antibody that recognizes an epitope of a CAPRIN-1 protein recognized by the anti-CAPRIN-1 antibody described above can be obtained by a method generally known to those skilled in the art. For example, the antibody can be obtained by a method which involves determining the epitope of the CAPRIN-1 protein recognized by the anti-CAPRIN-1 antibody by a conventional method (e.g., epitope mapping) and preparing an antibody using a polypeptide having an amino acid sequence contained in the epitope as an immunogen, or a method which involves determining an epitope for an antibody prepared by a conventional method and selecting an antibody that recognizes the same epitope as that for the anti-CAPRIN-1 antibody.

The antibody of the present invention has an affinity constant Ka ($k_{on}/k_{off}$) of preferably at least $10^7$ $M^{-1}$, at least $10^8$ $M^{-1}$, at least $5 \times 10^8$ $M^{-1}$, at least $10^9$ $M^{-1}$, at least $5 \times 10^9$ $M^{-1}$, at least $10^{10}$ $M^{-1}$, at least $5 \times 10^{10}$ $M^{-1}$, at least $10^{11}$ $M^{-1}$, at least $5 \times 10^{11}$ $M^{-1}$, at least $10^{12}$ $M^{-1}$, or at least $10^{13}$ M.

The antibody of the present invention can be conjugated with an antitumor agent. The conjugation of the antibody with the antitumor agent can be performed via a spacer having a group (e.g., a succinimidyl group, a formyl group, a 2-pyridyldithio group, a maleimidyl group, an alkoxycarbonyl group, or a hydroxy group) reactive with an amino group, a carboxyl group, a hydroxy group, a thiol group, or the like.

Examples of the antitumor agent include the following antitumor agents publicly known in literatures, etc.: paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethylenethiophosphoramide, trimethylolomelamine, bullatacin, bullatacinone, camptothecin, bryostatin, callystatin, cryptophycin 1, cryptophycin 8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, caminomycin, carzinophilin, chromomycin, dactinomycin, detorbicin, 6-diazo-5-oxo-L-norleucine, Adriamycin, epirubicin, esorubicin, idarubicin, marcellomycin, mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, androgens (e.g., calusterone, dromostanolone propionate, epitiostanol, mepitiostane, and testolactone), aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elformithine, elliptinium acetate, epothilone, etoglucid, lentinan, lonidamine, maytansine, ansamitocin, mitoguazone, mitoxantrone, mopidanmol, nitraerine, pentostatin, phenamet, pirarubicin, losoxantrone, podophyllinic acid, 2-ethylhydrazide, procarbazine, razoxane, rhizoxin, schizophyllan, spirogermanium, tenuazonic acid, triaziquone, roridin A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxantrone, vincristine, vinorelbine, novantrone, teniposide, edatrexate, daunomycin, aminopterin, Xeloda, ibandronate, irinotecan, topoisomerase inhibitors, difluoromethylornithine (DMFO), retinoic acid, capecitabine, and pharmaceutically acceptable salts and derivatives thereof.

Alternatively, the antibody of the present invention can be administered in combination with an antitumor agent to produce a higher therapeutic effect. This approach is adaptable to a patient with cancer expressing CAPRIN-1 either before or after surgical operation. This approach can be applied, particularly after surgery, to CAPRIN-1-expressing cancer, which has been treated conventionally with an antitumor agent alone, to produce higher prevention of cancer recurrence or prolongation of survival time.

Examples of the antitumor agent used in the combined administration with the antibody of the present invention include the following antitumor agents publicly known in literatures, etc.: paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethylenethiophosphoramide, trimethylolomelamine, bullatacin, bullatacinone, camptothecin, bryostatin, callystatin, cryptophycin 1, cryptophycin 8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, caminomycin, carzinophilin, chromomycin, dactinomycin, detorbicin, 6-diazo-5-oxo-L-norleucine, Adriamycin, epirubicin, esorubicin, idarubicin, marcellomycin, mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elformithine, elliptinium acetate, epothilone, etoglucid, lentinan, lonidamine, maytansine, ansamitocin, mitoguazone, mitoxantrone, mopidanmol, nitraerine, pentostatin, phenamet, pirarubicin, losoxantrone, podophyllinic acid, 2-ethylhydrazide, procarbazine, razoxane, rhizoxin, schizophyllan, spirogermanium, tenuazonic acid, triaziquone, roridin A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxantrone, vincristine, vinorelbine, novantrone, teniposide, edatrexate, daunomycin, aminopterin, Xeloda, ibandronate, irinotecan, topoisomerase inhibitors, difluoromethylornithine (DMFO), retinoic acid, capecitabine, and pharmaceutically acceptable salts (known in the art) and derivatives (known in the art) thereof. Of these antitumor agents, cyclophosphamide, paclitaxel, docetaxel, or vinorelbine is particularly preferably used.

Alternatively, the antibody of the present invention may be bound to a radioisotope publicly known in literatures, etc., such as $^{211}$At, $^{131}$I, $^{125}$I, $^{90}$Y, $^{186}$Re, $^{188}$Re, $^{153}$Sm, $^{212}$Bi, $^{32}$P, $^{175}$Lu, or $^{176}$Lu. Desirably, a radioisotope effective for the treatment or diagnosis of tumor is used.

The antibody of the present invention is an antibody having immunological reactivity with CAPRIN-1, an antibody specifically recognizing CAPRIN-1, or an antibody specifically binding to CAPRIN-1 and exhibits cytotoxic activity or antiproliferative effect on cancer. The antibody should have a structure that causes little or no rejection in recipient animals. Examples of such antibodies include human antibodies, humanized antibodies, chimeric antibodies (e.g., human-mouse chimeric antibodies), single-chain antibodies, and bispecific antibodies when the recipient animals are humans. These antibodies (1) have variable regions of heavy and light chains derived from a human antibody, (2) have variable regions with CDRs (CDR1, CDR2, and CDR3) of heavy and light chains derived from a non-human animal antibody and framework regions derived from a human antibody, or (3) these antibodies are recombinant antibodies having variable regions of heavy and light chains derived from a non-human animal antibody and heavy and light chain constant regions derived from a human antibody. The antibody of the present invention is preferably antibody (1) or (2).

Such recombinant antibodies can be prepared as follows: DNAs encoding monoclonal antibodies (e.g., human, mouse, rat, rabbit, and chicken monoclonal antibodies) against human CAPRIN-1 are cloned from antibody-producing cells such as hybridomas and used as templates in RT-PCR or the like to prepare DNAs encoding the variable regions of the light and heavy chains in the antibodies. The respective sequences of the variable regions of the light and heavy chains and the respective sequences of CDR1, CDR2, and CDR3 in each region are determined on the basis of the Kabat EU numbering system (Kabat et al., Sequences of Proteins of Immunological Interest, 5th Ed. Public Health Service, National Institute of Health, Bethesda, Md. (1991)).

Such a DNA encoding each variable region or a DNA encoding each CDR is prepared using a gene recombination technique (Sambrook et al., Molecular Cloning A Laboratory Manual, Cold Spring Harbor Laboratory Press (1989)) or a DNA synthesizer. In this context, the human monoclonal antibody-producing hybridomas can be prepared by immunizing human antibody-producing animals (e.g., mice) with human CAPRIN-1 and then fusing spleen cells excised from the immunized animals with myeloma cells. Aside from this, DNAs encoding light or heavy chain variable and constant regions derived from human antibody are prepared, if necessary, using a gene recombination technique or a DNA synthesizer.

The prepared recombinant DNAs can be incorporated into one or more appropriate vectors, which are then introduced into host cells (e.g., mammalian cells, yeast cells, and insect cells) so that the DNAs are (co)expressed to produce recombinant antibodies (P. J. Delves., ANTIBODY PRODUCTION ESSENTIAL TECHNIQUES., 1997 WILEY, P. Shepherd and C. Dean., Monoclonal Antibodies., 2000 OXFORD UNIVERSITY PRESS; and J. W. Goding., Monoclonal Antibodies: principles and practice., 1993 ACADEMIC PRESS).

Examples of the antibody of the present invention prepared by any of the methods described above include the following antibody (a) obtained in Examples described later:

(a) an antibody or the fragment thereof comprising a heavy chain variable region comprising amino acid sequences represented by SEQ ID NOs: 5, 6, and 7 and a light chain variable region comprising amino acid sequences represented by SEQ ID NOs: 9, 10, and 11 (e.g., an antibody composed of a heavy chain variable region consisting of the amino acid sequence represented by SEQ ID NO: 8 and a light chain variable region consisting of the amino acid sequence represented by SEQ ID NO: 12).

In this context, the amino acid sequences represented by SEQ ID NOs: 5, 6, and 7 correspond to CDR1, CDR2, and CDR3, respectively, of a heavy chain variable region of a mouse antibody. The amino acid sequences represented by SEQ ID NOs: 9, 10, and 11 correspond to CDR1, CDR2, and CDR3, respectively, of a light chain variable region of a mouse antibody.

Examples of the humanized antibody, the chimeric antibody, the single-chain antibody, or the multispecific antibody of the present invention include the following antibodies (i), (ii), and (iii):

(i) an antibody or the fragment thereof comprising a heavy chain variable region comprising the amino acid sequences represented by SEQ ID NOs: 5, 6, and 7 and the amino acid sequences of framework regions derived from human antibody and a light chain variable region comprising the amino acid sequences represented by SEQ ID NOs: 9, 10, and 11 and the amino acid sequences of framework regions derived from human antibody;

(ii) an antibody or the fragment thereof comprising a heavy chain variable region comprising the amino acid sequences represented by SEQ ID NOs: 5, 6, and 7 and the amino acid sequences of framework regions derived from human antibody, a heavy chain constant region comprising an amino acid sequence derived from human antibody, a light chain variable region comprising the amino acid sequences represented by SEQ ID NOs: 9, 10, and 11 and the amino acid sequences of framework regions derived from human antibody, and a light chain constant region comprising an amino acid sequence derived from human antibody; and (iii) an antibody or the fragment thereof comprising a heavy chain variable region comprising the amino acid sequence represented by SEQ ID NO: 8, a heavy chain constant region comprising an amino acid sequence derived from human antibody, a light chain variable region comprising the amino acid sequence represented by SEQ ID NO: 12, and a light chain constant region comprising an amino acid sequence derived from human antibody.

The sequences of the constant and variable regions of human antibody heavy and light chains are available from, for example, NCBI (USA; GenBank, UniGene, etc.). For example, the following sequences can be referred to: Accession No. J00228 for a constant region of a human IgG1 heavy chain; Accession No. J00230 for a constant region of a human IgG2 heavy chain; Accession No. X03604 for a constant region of a human IgG3 heavy chain; Accession No. K01316 for a constant region of a human IgG4 heavy chain; Accession Nos. V00557, X64135, and X64133 for a constant region of a human light chain κ; and Accession Nos. X64132 and X64134 for a constant region of a human light chain λ.

Preferably, these antibodies have cytotoxic activity and can thereby exert an antitumor effect.

The above particular sequences of the variable regions and CDRs of heavy and light chains in each antibody are provided merely for illustrative purposes. It is obvious that the antibody of the present invention is not limited by the particular sequences. Hybridomas capable of producing anti-human CAPRIN-1 human antibodies or non-human animal antibodies (e.g., mouse antibodies) different from those described above are prepared, and monoclonal antibodies produced by the hybridomas are recovered and assessed as being (or being not) the antibodies of interest with immunological binding activity against human CAPRIN-1 and cytotoxic activity as indexes. The monoclonal antibody-producing hybridomas of interest are thereby identified. Then, DNAs encoding variable regions heavy and light chains of the in antibodies of interest are produced from the hybridomas and sequenced, as described above. The DNAs are used for the preparation of the different antibodies.

The antibody described above may be the antibody (a) having the substitution, deletion, or addition of one or several amino acids, particularly in a sequence of a framework region and/or a constant region, as long as the antibody has such specificity that it can specifically recognize CAPRIN-1. In this context, the term "several" means preferably 2 to 5, more preferably 2 or 3.

The present invention further provides a DNA encoding the antibody of the present invention, a DNA encoding the heavy or light chain of the antibody, or a DNA encoding the variable region of the heavy or light chain in the antibody. Such a DNA includes, for example, a DNA encoding a heavy chain variable region which comprises nucleotide sequences encoding the amino acid sequences represented by SEQ ID NOs: 5, 6, and 7, and a DNA encoding a light chain variable region which comprises nucleotide sequences encoding the amino acid sequences represented by SEQ ID NOs: 9, 10, and 11, in the case of the antibody (a).

The CDRs encoded by the DNA having these sequences serve as regions that determine the specificity of the antibody. Sequences encoding the other regions (i.e., constant regions and framework regions) of the antibody may therefore be sequences derived from other antibodies. In this context, "other antibodies" also include antibodies derived from non-human organisms and are preferably those derived from humans from the viewpoint of reducing side effects. Specifically, the DNA of the present invention preferably comprises nucleotide sequences encoding corresponding human antibody-derived amino acid sequences of regions encoding each framework region and each constant region in the heavy and light chains.

Further examples of the DNA encoding the antibody of the present invention include a DNA encoding a heavy chain variable region which comprises a nucleotide sequence encoding the amino acid sequence represented by SEQ ID NO: 8, and a DNA encoding a light chain variable region which comprises a nucleotide sequence encoding the amino acid sequence represented by SEQ ID NO: 12. In this context, the nucleotide sequence encoding the amino acid sequence represented by SEQ ID NO: 8 is, for example, the nucleotide sequence represented by SEQ ID NO: 13. The nucleotide sequence encoding the amino acid sequence represented by SEQ ID NO: 12 is, for example, the nucleotide sequence represented by SEQ ID NO: 14. In such a DNA, a region encoding each constant region in the heavy and light chains should comprise a nucleotide sequence encoding a corresponding amino acid sequence derived from human antibody.

These antibody DNAs can be obtained, for example, by the methods described above or the following method: first, total RNAs are prepared from hybridomas related to the antibody of the present invention using a commercially available RNA extraction kit, and cDNAs are synthesized using reverse transcriptase and random primers or the like. Subsequently, the antibody-encoding cDNAs are amplified by PCR using oligonucleotide primers for conserved sequences of each variable region in known mouse antibody heavy and light chain genes. Sequences encoding the constant regions can be obtained by the PCR amplification of known sequences. The nucleotide sequence of the DNA can be incorporated into a plasmid or a phage for sequencing, for example, and determined according to a routine method.

The antitumor effect of the anti-CAPRIN-1 antibody used in the present invention on CAPRIN-1-expressing cancer cells seems to be brought about by effector cell-mediated antibody-dependent cellular cytotoxicity (ADCC) and complement-dependent cytotoxicity (CDC) against the CAPRIN-1-expressing cells.

The antitumor effect based on the mechanism is known to correlate with the number of antibody-binding target molecules expressed on the surface of cancer cells (Niwa R., Clinical Cancer Research 2005 Mar. 15; 11 (6): 2327-2336). The number of target molecules expressed on the surface of cancer cells can be examined using an existing assay kit capable of measuring the number of molecules on cell surface. Specifically, the number of antibody-binding target molecules can be determined by: reacting cancer cells with, for example, antibodies against the target molecules as primary antibodies; reacting therewith fluorescently labeled antibodies against the primary antibodies, together with calibration curve beads with the preliminarily known number of molecules; measuring the mean fluorescence intensity of the samples; and determining the number of the target molecules on the basis of the obtained calibration curve.

Thus, the anti-CAPRIN-1 antibody used in the present invention can be evaluated for its activity by determining ex vivo the ADCC activity or the CDC activity against CAPRIN-1-expressing cancer cells or by examining the number of CAPRIN-1 molecules expressed on the surface of cancer cells in the case of using the anti-CAPRIN-1 antibody according to the present invention as a primary antibody as specifically shown below in Examples.

The anti-CAPRIN-1 antibody used in the present invention binds to CAPRIN-1 proteins on cancer cells and exhibits an antitumor effect through the activity. Thus, the anti-CAPRIN-1 antibody of the present invention is presumably useful in the treatment or prevention of cancer. Specifically, the present invention provides a pharmaceutical composition for treatment and/or prevention of cancer, comprising the anti-CAPRIN-1 antibody as an active ingredient. The anti-CAPRIN-1 antibody used for the purpose of administration to human bodies (antibody therapy) is preferably a human antibody or a humanized antibody for reducing immunogenicity.

The anti-CAPRIN-1 antibody with higher binding affinity for a CAPRIN-1 protein on cancer cell surface exerts stronger antitumor activity. Thus, a stronger antitumor effect can be expected if the anti-CAPRIN-1 antibody having high binding affinity for the CAPRIN-1 protein can be obtained. Such an antibody is adaptable to a pharmaceutical composition intended for the treatment and/or prevention of cancer. Desirably, such high binding affinity is preferably at least $10^7$ $M^{-1}$, at least $10^8$ $M^{-1}$, at least $5 \times 10^8$ $M^{-1}$, at least $10^9$ $M^{-1}$, at least $5 \times 10^9$ $M^{-1}$, at least $10^{10}$ $M^{-1}$, at least $5 \times 10^{10}$ $M^{-1}$, at least $10^{11}$ $M^{-1}$, at least $5 \times 10^{11}$ $M^{-1}$, at least $10^{12}$ $M^{-1}$, or at least $10^{13}$ $M^{-1}$, in terms of an association constant (affinity constant) Ka ($k_{on}/k_{off}$), as described above.

The binding of anti-CAPRIN-1 antibodies to a larger number of CAPRIN-1 molecules on cancer cell surface produces stronger antitumor activity. Desirably, the number of CAPRIN-1 molecules to which the antibodies bind for the expected antitumor effect is $10^4$ or more, preferably $10^5$ or more CAPRIN-1 molecules per cancer cell measured using the anti-CAPRIN-1 antibody of the present invention.

<Binding to Antigen-Expressing Cells>

The ability of the antibody to bind to CAPRIN-1 can be determined by use of binding assay using, for example, ELISA, Western blot, immunofluorescence, and flow cytometry analysis, as described in Examples.

<Immunohistochemical Staining>

The antibody that recognizes CAPRIN-1 can be tested for its reactivity with CAPRIN-1 by an immunohistochemical method well known to those skilled in the art using a paraformaldehyde- or acetone-fixed frozen section or paraformaldehyde-fixed paraffin-embedded section of a tissue obtained from a patient during surgical operation or from an animal carrying a xenograft tissue inoculated with a cell line expressing CAPRIN-1 either spontaneously or after transfection.

For immunohistochemical staining, the antibody reactive with CAPRIN-1 can be stained by various methods. For example, the antibody can be visualized through reaction with a horseradish peroxidase-conjugated goat anti-mouse antibody, goat anti-rabbit antibody or goat anti-chicken antibody.

<Pharmaceutical Composition>

A target of the pharmaceutical composition for treatment and/or prevention of cancer of the present invention is not particularly limited as long as the target is cancer (cells) expressing a CAPRIN-1 gene.

The terms "tumor" and "cancer" used herein mean malignant neoplasm and are used interchangeably with each other.

The cancer targeted in the present invention is cancer expressing a CAPRIN-1 protein-encoding gene and is preferably breast cancer, kidney cancer, pancreatic cancer, large bowel cancer, lung cancer, brain tumor, gastric cancer, uterine cervix cancer, ovary cancer, prostate cancer, urinary bladder cancer, esophageal cancer, leukemia, lymphoma, fibrosarcoma, mastocytoma, or melanoma.

Specific examples of these cancers include, but not limited to, breast adenocarcinoma, complex-type breast adenocarcinoma, malignant mixed tumor of mammary gland, intraductal papillary adenocarcinoma, lung adenocarcinoma, squamous cell cancer, small-cell cancer, large-cell cancer, glioma which is tumor of neuroepithelial tissue, ependymoma, neuronal tumor, embryonal neuroectodermal tumor, neurilemmoma, neurofibroma, meningioma, chronic lymphocytic leukemia, lymphoma, gastrointestinal lymphoma, alimentary lymphoma, small to medium cell-type lymphoma, cecal cancer, ascending colon cancer, descending colon cancer, transverse colon cancer, sigmoid colon cancer, rectal cancer, epithelial ovarian cancer, germ cell tumor, stromal cell tumor, pancreatic ductal carcinoma, invasive pancreatic ductal carcinoma, pancreatic adenocarcinoma, acinar cell carcinoma, adenosquamous carcinoma, giant cell tumor, intraductal papillary-mucinous neoplasm, mucinous cystic neoplasm, pancreatoblastoma, serous cystadenocarcinoma, solid-pseudopapillary tumor, gastrinoma, glucagonoma, insulinoma, multiple endocrine neoplasia type-1 (Wermer's syndrome), nonfunctional islet cell tumor, somatostatinoma, and VIPoma.

The test subject as the recipient are preferably mammals, for example, mammals including primates, pet animals, livestock, and sport animals and are particularly preferably humans, dogs, and cats.

In the case of using the antibody of the present invention as a pharmaceutical composition, the pharmaceutical composition can be formulated by a method generally known to those skilled in the art. For example, the pharmaceutical composition can be used in the form of a parenteral injection of an aseptic solution or suspension with water or any other pharmaceutically acceptable liquid. For example, the pharmaceutical composition may be formulated with the antibody mixed in a unit dosage form required for generally accepted pharmaceutical practice, in appropriate combination with pharmacologically acceptable carriers or media, specifically, sterilized water, physiological saline, plant oil, an emulsifier, a suspending agent, a detergent, a stabilizer, a flavoring agent, an excipient, a vehicle, a preservative, a binder, etc. The amount of the active ingredient in such a preparation is determined so that an appropriate dose within the prescribed range can be achieved.

An aseptic composition for injection can be formulated according to conventional pharmaceutical practice using a vehicle such as injectable distilled water.

Examples of aqueous solutions for injection include physiological saline, isotonic solutions containing glucose and other adjuvants, for example, D-sorbitol, D-mannose, D-mannitol, and sodium chloride. These solutions may be used in combination with an appropriate solubilizer, for example, an alcohol (specifically, ethanol) or a polyalcohol (e.g., propylene glycol and polyethylene glycol), or a nonionic detergent, for example, polysorbate 80 ™ or HCO-60.

Examples of oily solutions include sesame oil and soybean oil. These solutions may be used in combination with a solubilizer such as benzyl benzoate or benzyl alcohol. The solutions may be further mixed with a buffer (e.g., a phosphate buffer solution and a sodium acetate buffer solution), a soothing agent (e.g., procaine hydrochloride), a stabilizer (e.g., benzyl alcohol and phenol), and an antioxidant. The injection solutions thus prepared are usually charged into appropriate ampules.

The pharmaceutical composition of the present invention is administered orally or parenterally, preferably parenterally.

Specific examples of its dosage forms include injections, intranasal administration agents, transpulmonary administration agents, and percutaneous administration agents. Examples of the injections include intravenous injection, intramuscular injection, intraperitoneal injection, and subcutaneous injection, through which the pharmaceutical composition can be administered systemically or locally.

Also, the administration method can be appropriately selected depending on the age, weight, sex, symptoms, etc. of a patient. The dose of a pharmaceutical composition containing the antibody or a polynucleotide encoding the antibody can be selected within a range of, for example, 0.0001 to 1000 mg/kg of body weight per dose. Alternatively, the dose can be selected within a range of, for example, 0.001 to 100000 mg/body of a patient, though the dose is not necessarily limited to these numeric values. Although the dose and the administration method vary depending on the weight, age, sex, symptoms, etc. of a patient, those skilled in the art can appropriately select the dose and the method.

The pharmaceutical composition including the antibody or fragments thereof of the present invention can be administered to a test subject to treat and/or prevent cancer, preferably breast cancer, kidney cancer, pancreatic cancer, large bowel cancer, lung cancer, brain tumor, gastric cancer, uterine cervix cancer, ovary cancer, prostate cancer, urinary bladder cancer, esophageal cancer, leukemia, lymphoma, fibrosarcoma, mastocytoma, or melanoma.

The present invention further encompasses a method for treating and/or preventing cancer, comprising administering the pharmaceutical composition of the present invention in combination with the antitumor agent as exemplified above or a pharmaceutical composition comprising the antitumor agent to a test subject. The antibody or the fragment thereof of the present invention may be administered simultaneously with or separately from the antitumor agent to the test subject. In the case of separately administering these pharmaceutical compositions, either one may be administered first or later. Their dosing intervals, doses, administration routes, and the number of doses can be appropriately selected by a specialist. The dosage forms of separate drugs to be administered simultaneously also include, for example, pharmaceutical compositions each formulated by mixing the antibody or the fragment thereof of the present invention and the antitumor agent into a pharmacologically acceptable carrier (or medium). The above descriptions about prescription, formulation, administration routes, doses, cancer, etc. as to the pharmaceutical compositions and dosage forms containing the antibody of the present invention are also applicable to any of the above-described pharmaceutical compositions and dosage forms containing the antitumor agent.

Thus, the present invention also provides a pharmaceutical combination for treatment and/or prevention of cancer, comprising the pharmaceutical composition of the present invention and a pharmaceutical composition comprising the antitumor agent as exemplified above. The present invention also provides a pharmaceutical composition for treatment and/or prevention of cancer, comprising the antibody or the fragment thereof of the present invention and the antitumor agent together with a pharmacologically acceptable carrier.

<Polypeptide and DNA>

The present invention further provides the following polypeptides and DNAs related to the antibody (a):

(i) a polypeptide comprising the amino acid sequences represented by SEQ ID NOs: 8 and 12, and a DNA encoding the polypeptide, for example, a DNA comprising the nucleotide sequences represented by SEQ ID NOs: 13 and 14;

(ii) a heavy chain CDR polypeptide selected from the group consisting of amino acid sequences represented by SEQ ID NOs: 5, 6, and 7, and a DNA encoding the polypeptide; and (iii) a light chain CDR polypeptide selected from the group consisting of amino acid sequences represented by SEQ ID NOs: 9, 10, and 11, and a DNA encoding the polypeptide.

These polypeptides and DNAs can be prepared using gene recombination techniques as described above.

SUMMARY OF THE PRESENT INVENTION

The aspects of the present invention described above are summarized below.

(1) An antibody or a fragment thereof which has immunological reactivity with a CAPRIN-1 protein, the antibody or the fragment thereof comprising a heavy chain variable region comprising CDRs of SEQ ID NOs: 5, 6, and 7 and a light chain variable region comprising CDRs of SEQ ID NOs: 9, 10, and 11.

(2) The antibody or the fragment thereof according to (1), wherein the antibody is a human antibody, a humanized antibody, a chimeric antibody, a single-chain antibody, or a bispecific antibody.

(3) The antibody or the fragment thereof according to (1) or (2), wherein the antibody or the fragment thereof is conjugated with an antitumor agent.

(4) A pharmaceutical composition for treatment and/or prevention of cancer comprising an antibody or the fragment thereof as an active ingredient, wherein the antibody comprises a heavy chain variable region comprising CDRs of SEQ ID NOs: 5, 6, and 7 and a light chain variable region comprising CDRs of SEQ ID NOs: 9, 10, and 11 and has immunological reactivity with the CAPRIN-1 protein.

(5) The pharmaceutical composition according to (4), wherein the cancer is breast cancer, kidney cancer, pancreatic cancer, large bowel cancer, lung cancer, brain tumor, gastric cancer, uterine cervix cancer, ovary cancer, prostate cancer, urinary bladder cancer, esophageal cancer, leukemia, lymphoma, fibrosarcoma, mastocytoma, or melanoma.

(6) A pharmaceutical combination for treatment and/or prevention of cancer, comprising a pharmaceutical composition according to (4) or (5) and a pharmaceutical composition comprising an antitumor agent.

(7) A DNA encoding an antibody or a fragment thereof according to (1) or (2).

(8) A method for treating and/or preventing cancer, comprising administering an antibody or a fragment thereof according to any of (1) to (3), a pharmaceutical composition according to (4) or (5), or a pharmaceutical combination according to (6) to a test subject.

EXAMPLES

Hereinafter, the present invention will be described specifically with reference to Examples. However, the scope of the present invention is not intended to be limited by these specific examples.

Example 1

Analysis of CAPRIN-1 Gene Expression in Each Tissue

Gene expression of CAPRIN-1 in canine and human normal tissues and various cell lines was examined by RT-PCR according to Example 1(4) described in WO2010/016526. As a result, strong expression was observed in the testis among the healthy canine tissues, whereas expression was observed in canine breast cancer and adenocarcinoma tissues. As a result of also confirming the expression in human tissues, the expression was confirmed only in the testis among normal tissues, as with the canine CAPRIN-1 gene. By contrast, the expression was detected in many types of cancer cell lines, including 8 human breast cancer cell lines (ZR75-1, MCF7, T47D, SK-BR-3, MDA-MB-157, BT-20, MDA-MB-231V, and MRK-nu-1) and 4 pancreatic cancer cell lines (Capan-2, MIAPaCa-2, Panc-1, and BxPc-3), among cancer cells. These results demonstrated that CAPRIN-1 is expressed in various cancer cells, though its expression is not seen in normal tissues other than the testis.

Example 2

Preparation of Mouse Monoclonal Antibody Against CAPRIN-1

100 μg of human CAPRIN-1 proteins having the amino acid sequence of SEQ ID NO: 2, which were prepared in Example 3 described in WO2010/016526, was mixed with an equal amount of MPL+TDM adjuvant (Sigma-Aldrich Corp.). This mixture was used as an antigen solution per mouse. The antigen solution was intraperitoneally administered to each 6-week-old Balb/c mouse (Japan SLC, Inc.). Then, 7 boosters were performed every 1 week to complete immunization. Three days after the final shot, the spleen of each mouse was excised and ground between two sterilized glass slides. Procedures of washing with PBS(−) (Nissui Pharmaceutical Co., Ltd.) and removing the supernatant by centrifugation at 1500 rpm for 10 minutes were repeated three times to obtain spleen cells. The obtained spleen cells were mixed with mouse myeloma cells SP2/0 (purchased from ATCC) at a ratio of 10:1. 200 μl of an RPMI1640 medium containing 10% FBS was heated to 37° C. and mixed with 800 μl of PEG 1500 (Boehringer Ingelheim GmbH), and the PEG solution thus prepared was added to the cell mixture, which was then left standing for 5 minutes for cell fusion. After removal of the supernatant by centrifugation at 1700 rpm for 5 minutes, the cells were suspended in 150 ml of an RPMI1640 medium containing 15% FBS supplemented with 2% equivalent of a HAT solution (Life Technologies, Inc./ Gibco) (HAT selective medium). This suspension was inoculated to fifteen 96-well plates (Thermo Fisher Scientific Inc./ Nunc) at a concentration of 100 μl/well. The spleen cells and the myeloma cells were fused by culture at 37° C. for 7 days under conditions of 5% $CO_2$ to obtain hybridomas.

The prepared hybridomas were screened with the binding affinity of antibodies produced by the hybridomas against CAPRIN-1 proteins as an index. One μg/ml solution of the CAPRIN-1 proteins prepared in Example 3 described in WO2010/016526 was added to a 96-well plate at a concentration of 100 μl/well and left standing at 4° C. for 18 hours. Each well was washed three times with PBS-T. Then, a 0.5% bovine serum albumin (BSA) solution (Sigma-Aldrich Corp.) was added thereto at a concentration of 400 μl/well and left standing at room temperature for 3 hours. The solution in each well was discarded, and each well was washed three times with 400 μl of PBS-T. Then, the culture supernatant of each hybridoma obtained above was added thereto at a concentration of 100 μl/well and left standing at room temperature for 2 hours. Each well was washed three times with PBS-T. Then, HRP-labeled anti-mouse IgG (H+L) antibodies (Invitrogen Corp.) diluted 5000-fold with PBS were added thereto at a concentration of 100 μl/well and left standing at room temperature for 1 hour. Each well was washed three times with PBS-T. Then, a TMB substrate solution (Thermo Fisher Scientific Inc.) was added thereto at a concentration of 100 and left standing for 15 to 30 minutes to cause color reaction. After the color development, the reaction was terminated by the addition of 1 N sulfuric acid at a concentration of 100 μl/well. The absorbance was measured at 450 nm and 595 nm using an absorption spectrometer. As a result, several hybridomas producing antibodies having high absorbance were selected.

The selected hybridomas were added to a 96-well plate at a density of 0.5 cells/well and cultured in the plate. One week later, hybridomas forming single colonies in the wells were observed. The cells in these wells were further cultured, and the cloned hybridomas were screened with the binding affinity of antibodies produced by the hybridomas against CAPRIN-1 proteins as an index. One μg/ml solution of the CAPRIN-1 proteins prepared in Example 3 described in WO2010/016526 was added to a 96-well plate at a concentration of 100 μL/well and left standing at 4° C. for 18 hours. Each well was washed three times with PBS-T. Then, a 0.5% BSA solution was added thereto at a concentration of 400 μL/well and left standing at room temperature for 3 hours. The solution in each well was discarded, and each well was washed three times with 400 μL of PBS-T. Then, the culture supernatant of each hybridoma obtained above was added thereto at a concentration of 100 μL/well and left standing at room temperature for 2 hours. Each well was washed three times with PBS-T. Then, HRP-labeled anti-mouse IgG (H+L) antibodies (Invitrogen Corp.) diluted 5000-fold with PBS were added thereto at a concentration of 100 μl/well and left standing at room temperature for 1 hour. Each well was washed three times with PBS-T. Then, a TMB substrate solution (Thermo Fisher Scientific Inc.) was added thereto at a concentration of 100 μl/well and left standing for 15 to 30 minutes to cause color reaction. After the color development, the reaction was terminated by the addition of 1 N sulfuric acid at a concentration of 100 μl/well. The absorbance was measured at 450 nm and 595 nm using an absorption spectrometer. As a result, 112 hybridoma lines producing monoclonal antibodies reactive with CAPRIN-1 proteins were obtained.

Next, these monoclonal antibodies were screened for antibodies reactive with the surface of breast cancer cells expressing CAPRIN-1. Specifically, $10^6$ cells of a human breast cancer cell line MDA-MB-231V were centrifuged in a 1.5-mL microcentrifuge tube. 100 μL of the culture supernatant of each hybridoma obtained above was added thereto and left standing for 1 hour on ice. After washing with PBS, FITC-labeled goat anti-mouse IgG antibodies (Invitrogen Corp.) diluted 500-fold with PBS containing 0.1% FBS were added thereto and left standing for 1 hour on ice. After washing with PBS, the fluorescence intensity was measured using FACS Calibur (Becton, Dickinson and Company). On the other hand, the same operation as above was performed using the serum of each untreated 6-week-old Balb/c mouse diluted 500-fold with a medium for hybridoma culture, instead of the antibodies, to prepare a control. As a result, one monoclonal antibody (#1) having stronger fluorescence intensity than that of the control, i.e., reactive with the surface of breast cancer cells, was selected.

Example 3

Characterization of Selected Monoclonal Antibody

The monoclonal antibodies obtained in Example 2 were analyzed according to a method described in Example 5 of WO2010/016526 for their nucleotide sequences and amino acid sequences encoded thereby. As the result, the monoclonal antibody #1 was composed of a heavy chain variable region consisting of the amino acid sequence represented by SEQ ID NO: 8 and a light chain variable region consisting of the amino acid sequence represented by SEQ ID NO: 12. The resulting nucleotide sequence encoding the heavy chain variable region of the monoclonal antibody #1 is shown in SEQ ID NO: 13, and the amino acid sequence is shown in SEQ ID NO: 8. The nucleotide sequence encoding the light chain variable region thereof is shown in SEQ ID NO: 14, and the amino acid sequence is shown in SEQ ID NO: 12.

Specifically, the monoclonal antibody #1 was confirmed to consist of the heavy chain variable region consisting of the amino acid sequence represented by SEQ ID NO: 8 and the light chain variable region consisting of the amino acid sequence represented by SEQ ID NO: 12, wherein the heavy chain variable region had CDR1, CDR2, and CDR3 consisting of amino acid sequences of SEQ ID NOs: 5, 6, and 7, respectively, and the light chain variable region had CDR1, CDR2, and CDR3 consisting of amino acid sequences of SEQ ID NOs: 9, 10, and 11, respectively.

Example 4

Preparation of Human-Mouse Chimeric Monoclonal Antibody

Both ends of the gene amplification fragment comprising the nucleotide encoding the heavy chain variable region of the mouse monoclonal antibody #1 obtained in Example 3, which consists of a nucleotide sequence represented by SEQ ID NO: 13, was treated with restriction enzymes, then purified, and inserted according to a routine method into a pcDNA4/myc-His vector (Invitrogen Corp.) already having gene inserts of a mouse antibody-derived leader sequence and a human IgG$_1$ H chain constant region comprising SEQ ID NO: 37. Also, the gene amplification fragment comprising the gene of the light chain variable region of the mouse monoclonal antibody #1 consisting of a nucleotide sequence represented by SEQ ID NO: 14 was treated at both ends with restriction enzymes, then purified, and inserted according to a routine method into a pcDNA3.1/myc-His (Invitrogen Corp.) vector already having gene inserts of a mouse antibody-derived leader sequence and a human IgG$_1$ L chain constant region comprising SEQ ID NO: 38.

Next, the recombinant vector having the insert of the heavy chain variable region (SEQ ID NO: 13) of the mouse monoclonal antibody #1 and the recombinant vector having the insert of the light chain variable region (SEQ ID NO: 14) of the mouse monoclonal antibody #1 were introduced into CHO-K1 cells (obtained from Riken Cell Bank). Specifically, $2\times10^5$ CHO-K1 cells were cultured in a Ham's F12 medium (Invitrogen Corp.) containing 1 mL of 10% FBS per well of a 12-well culture plate, and washed with PBS(−). Then, a fresh Ham's F12 medium containing 1 mL of 10% FBS per well was added thereto. 250 ng each of the vectors lysed in 30 µL of OptiMEM (Invitrogen Corp.) was mixed with 30 µL of Polyfect transfection reagent (Qiagen N.V.), and this mixture was added to each well. The CHO-K1 cells cotransfected with the recombinant vectors were cultured in a Ham's F12 medium containing 10% FBS supplemented with 200 µg/mL Zeocin (Invitrogen Corp.) and 200 µg/mL Geneticin (Roche Diagnostics K.K.) and then inoculated to a 96-well plate at a density of 0.5 cells/well to prepare a cell line stably producing a human-mouse chimeric monoclonal antibody #1 (#1) having the variable regions of the mouse monoclonal antibody #1.

Each prepared cell line was cultured for 5 days in a 150-cm$^2$ flask at a density of $5\times10^5$ cells/mL using 30 mL of a serum-free OptiCHO medium (Invitrogen Corp.) to obtain culture supernatants containing human-mouse chimeric monoclonal antibody #1.

Also, cell lines stably producing human-mouse chimeric comparative monoclonal antibodies 1 to 11 were prepared in the same way as above using the following anti-CAPRIN-1 mouse-derived monoclonal antibodies described in WO2010/016526 as comparative antibodies: a comparative antibody 1 consisting of the heavy chain variable region of SEQ ID NO: 15 and the light chain variable region of SEQ ID NO: 16; a comparative antibody 2 consisting of the heavy chain variable region of SEQ ID NO: 17 and the light chain variable region of SEQ ID NO: 18; a comparative antibody 3 consisting of the heavy chain variable region of SEQ ID NO: 19 and the light chain variable region of SEQ ID NO: 20; a comparative antibody 4 consisting of the heavy chain variable region of SEQ ID NO: 21 and the light chain variable region of SEQ ID NO: 22; a comparative antibody 5 consisting of the heavy chain variable region of SEQ ID NO: 23 and the light chain variable region of SEQ ID NO: 24; a comparative antibody 6 consisting of the heavy chain variable region of SEQ ID NO: 25 and the light chain variable region of SEQ ID NO: 26; a comparative antibody 7 consisting of the heavy chain variable region of SEQ ID NO: 27 and the light chain variable region of SEQ ID NO: 28; a comparative antibody 8 consisting of the heavy chain variable region of SEQ ID NO: 29 and the light chain variable region of SEQ ID NO: 30; a comparative antibody 9 consisting of the heavy chain variable region of SEQ ID NO: 31 and the light chain variable region of SEQ ID NO: 32; a comparative antibody 10 consisting of the heavy chain variable region of SEQ ID NO: 33 and the light chain variable region of SEQ ID NO: 34; and a comparative antibody 11 consisting of the heavy chain variable region of SEQ ID NO: 35 and the light chain variable region of SEQ ID NO: 36. Each prepared cell line was cultured for 5 days in a 150-cm$^2$ flask at a density of $5\times10^5$ cells/mL using 30 mL of a serum-free OptiCHO medium (Invitrogen Corp.) to obtain culture supernatants containing any of human-mouse chimeric comparative antibodies 1 to 11.

Example 5

Expression of CAPRIN-1 on Surface of Various Cancer Cells Using Anti-CAPRIN-1 Antibody #1

Next, the human breast cancer cell lines (ZR75-1, MCF7, T47D, SK-BR-3, MDA-MB-157, BT-20, MDA-MB-231V, and MRK-nu-1), the kidney cancer cell lines (Caki-1, Caki-2, A498, and ACHN), the urinary bladder cancer cell line (T24), the ovary cancer cell line (SKOV3), the lung cancer cell lines (QG56 and A549), the pancreatic cancer cell lines (Capan-2 and MIAPaCa-2), the prostate cancer cell line (PC3), the uterine cervix cancer cell line (SW756), the fibrosarcoma cell line (HT1080), the brain tumor cell lines (T98G, U87MG, U251, SNB19, and U373), the gastric cancer cell lines (MNK28 and MNK45), the large bowel cancer cell lines (HT29, Lovo, CaCo2, SW480, and HCT116), the leukemia cell line (AML5), and the lymphoma cell line (Ramos) confirmed to have CAPRIN-1 gene expression were examined for their expression of CAPRIN-1 proteins on the cell surface using the culture supernatants containing #1 obtained in Example 4. $5\times10^5$ cells of each cell line were centrifuged in each 1.5-mL microcentrifuge tube. Each culture supernatant (100 μL) containing the antibody #1 was added to the tube and left standing for 1 hour on ice. After washing with PBS, FITC-labeled goat anti-mouse IgG (H+L) antibodies (Jackson ImmunoResearch Laboratories, Inc.) diluted with PBS containing 0.1% FBS were added thereto and left standing at 4° C. for 30 minutes. After washing with PBS, the fluorescence intensity was measured using FACS Calibur (Becton, Dickinson and Company). The negative control used was cells reacted only with secondary antibodies. As a result, the cells supplemented with the antibody #1 had fluorescence intensity at least 35% stronger than that of the negative control. This demonstrated that CAPRIN-1 proteins are expressed on the cell membrane surface of the human cancer cell lines. The above rate of enhancement in fluorescence intensity was indicated by the rate of increase in mean fluorescence intensity (MFI) in each cell line and calculated according to the following expression:

Rate of increase in mean fluorescence intensity (Rate of enhancement in fluorescence intensity) (%)= ((MFI of cells reacted with the anti-CAPRIN-1 antibodies)−(Control MFI))/(Control MFI)×100.

Example 6

Antitumor Effect (ADCC Activity) of Anti-CAPRIN-1 Antibody on Cancer Cell

The anti-CAPRIN-1 human-mouse chimeric monoclonal antibody #1 obtained in Example 4 was studied for its ability to damage CAPRIN-1-expressing cancer cells by ADCC activity assay. The culture supernatant of the cells producing #1 was purified using Hitrap Protein A Sepharose FF (GE Healthcare Bio-Sciences Ltd.). After replacement with PBS (−), the solution was filtered through a 0.22-μm filter (Millipore Corp.). The resulting antibody was used for activity assay. $10^6$ cells each of the human breast cancer cell line MCF7, the human large bowel cancer cell line HCT-116, the human pancreatic cancer cell line MIAPaCa-2, the human kidney cancer cell line Caki-2, and the human lung cancer cell line QG56 confirmed to have CAPRIN-1 expression were collected into a 50-mL centrifuge tube, to which 100 μCi of chromium 51 was then added, followed by incubation at 37° C. for 2 hours. Then, the cells were washed three times with an RPMI 1640 medium containing 10% FBS and added at a density of $2\times10^3$ cells/well to each 96-well V-bottom plate to prepare target cells. The purified antibody #1 and the human-mouse chimeric comparative antibodies 1 to 11 obtained in Example 4 were each added thereto at a concentration of 1 μg/well. A cell population containing human NK cells separated using a routine method from human peripheral blood lymphocytes was added to the plate at a density of $2\times10^5$ cells/well and cultured at 37° C. for 4 hours under conditions of 5% $CO_2$. After the culture, the amount of chromium 51 released from damaged tumor cells was measured in the culture supernatant to calculate the cytotoxic activity of each anti-CAPRIN-1 antibody against the cancer cells. The negative control used was cells supplemented with isotype control antibodies. The cell population containing NK cells that was used in this evaluation was prepared as follows: human peripheral blood mononuclear cells separated from human peripheral blood according to a routine method using a specific gravity separation solution Histopaque for human peripheral blood mononuclear cell separation (Sigma-Aldrich Corp.) were reacted with various FITC-labeled antibodies (anti-human CD3 antibody, anti-human CD20 antibody, anti-human CD19 antibody, anti-human CD11c antibody, and anti-HLA-DR antibody (Becton, and Dickinson and Company)), and a cell population unstained with the antibodies was separated using a cell sorter (FACS Vantage SE (Becton, and Dickinson and Company)) or human NK cell separation kit (Miltenyi Biotec K.K.). As a result of evaluating cytotoxic activity against the cancer cells, the isotype control antibodies used and the comparative antibodies 1 to 11 used had cytotoxic activity less than 5% against all the cell lines. By contrast, the antibody #1 exhibited cytotoxic activity of 20%, 17%, 27%, 21%, and 10% against the human breast cancer cell line MCF7, the human large bowel cancer cell line HCT-116, the human pancreatic cancer cell line MIAPaCa-2, the human kidney cancer cell line Caki-2, and the human lung cancer cell line QG56, respectively. Likewise, the isotype control antibodies used and the comparative antibodies 1 to 11 used had cytotoxic activity less than 4% against all other cancer cells, breast cancer cell lines ZR75-1, T47D, Hs578T, 8T-20, SK-BR-3, MDA-MB-231V, and MRK-nu-1, glioma cell lines T98G and U373, a lung cancer cell line A549, kidney cancer cell lines Caki-1 and ACHN, a uterine cervix cancer cell line SW756, a urinary bladder cancer cell line T24, gastric cancer cell lines MKN28 and MKN45, a large bowel cancer cell line SW480, a leukemia cell line AML5, and a lymphoma cell line Ramos. By contrast, the antibody #1 was confirmed to have 10% or higher cytotoxic activity against these cell lines. These results showed that the obtained monoclonal antibody #1 against CAPRIN-1 damages CAPRIN-1-expressing cancer cells through its ADCC activity, and demonstrated that the antibody #1 exhibits stronger cytotoxic activity against human cancer cells than that of the comparative antibodies 1 to 11.

These results about cytotoxic activity were obtained by mixing the antibody against CAPRIN-1 used in the present invention, lymphocyte cells (population containing NK cells), and $2\times10^3$ cells of each cancer cell line with incorporated chromium 51, as described above, followed by culturing the cells for 4 hours, after the culture, measuring the amount of chromium 51 released into the medium, and calculating the cytotoxic activity against each cancer cell line according to the following expression.

Expression: Cytotoxic activity(%)=Amount of chromium 51 released from the target cells supplemented with the antibody against CAPRIN-1 and lymphocyte cells(population containing NK cells)/Amount of chromium 51 released from target cells supplemented with 1 N hydrochloric acid×100.

Next, the human-mouse chimeric monoclonal antibody #1 obtained in Example 4 was evaluated for its antitumor effect on cancer-bearing mice in vivo. The antibody used was column-purified from the culture supernatant of each cell line producing the antibody #1. Similarly, the anti-CAPRIN-1 antibodies human-mouse chimeric comparative monoclonal antibodies 1 to 11 prepared in Example 4 were also evaluated for their antitumor effects on cancer-bearing mice in vivo.

The antibody #1 was studied for its antitumor effect using cancer-bearing mice in which a CAPRIN-1-expressing human-derived cancer cell line was transplanted. $2\times10^6$ human pancreatic cancer cell line Capan-2 cells (purchased from ATCC) per mouse were subcutaneously transplanted into the backs of 65 Balb/c nude mice (Japan SLC, Inc.) and grown until the size of tumor became approximately 5 mm in diameter. The antibody #1 and the human-mouse chimeric comparative antibodies 1 to 11 were each intraperitoneally administered at a dose of 200 μg (200 μl)/mouse to 5 (per antibody) of these cancer-bearing mice. Then, each antibody was intraperitoneally administered to the cancer-bearing mice at the same dose as above a total of three times for 2 days. The size of tumor was measured every day, and the antitumor effect was observed. On the other hand, PBS(−) was administered instead of the antibodies to the remaining 5 cancer-bearing mice, which were in turn used as a control group. The size of tumor was calculated in terms of volume according to the expression 0.5×(Major axis×Minor axis× Minor axis).

As a result of observing the antitumor effect, the tumor size was reduced to approximately 85% in the mice that received the human-mouse chimeric comparative antibodies 1 to 11, whereas the antibody #1 exhibited an antitumor effect of reducing the tumor size to 80% in the test group that received the antibody #1 against CAPRIN-1, at day 29 after the antibody administration (with the tumor size in the control group at the same date defined as 100%). These results also demonstrated that the antibody #1 exerts a stronger in vivo antitumor effect than that of the comparative antibodies 1 to 11.

Example 7

The Number of CAPRIN-1 Molecules on Surface of Various Cancer Cells Recognized by Anti-CAPRIN-1 Antibody #1

Human breast cancer cell lines (ZR75-1, MCF7, T47D, SK-BR-3, MDA-MB-157, BT-20, MDA-MB-231V, and MRK-nu-1), kidney cancer cell lines (Caki-1, Caki-2, A498, and ACHN), a urinary bladder cancer cell line (T24), an ovary cancer cell line (SKOV3), lung cancer cell lines (QG56 and A549), pancreatic cancer cell lines (MIAPaCa-2 and Capan-2), a prostate cancer cell line (PC3), a uterine cervix cancer cell line (SW756), a fibrosarcoma cell line (HT1080), brain tumor cell lines (T98G, U87MG, U251, SNB19, and U373), gastric cancer cell lines (MNK28 and MNK45), large bowel cancer cell lines (HT29, Lovo, CaCo2, SW480, and HCT116), a leukemia cell line (AML5), and a lymphoma cell line (Ramos) were examined using an assay kit QIFIKIT for the number of molecules (Dako Japan Inc.) for the number of CAPRIN-1 molecules on their cell surface recognized by the anti-CAPRIN-1 antibody #1. Similarly, the number of CAPRIN-1 molecules on the surface of these various cancer cells was also examined using the comparative antibodies 1 to 11, which are anti-CAPRIN-1 monoclonal antibodies prepared in Example 4.

According to the protocol attached to the kit, the antibody #1 and comparative antibodies 1 to 11 were diluted into 5 μg/mL (in terms of final concentration) with PBS, and this dilution was added to each cell line and reacted for 30 minutes. After washing with PBS, fluorescently labeled anti-mouse IgG antibodies attached to the kit were added as secondary antibodies, together with calibration beads attached to the kit, to each cell line and left standing for 45 minutes on ice. Each cell line and the calibration beads were washed with PBS. Then, the fluorescence intensity was measured using FACS Calibur (Becton, Dickinson and Company) to obtain a mean fluorescence intensity value (mean). Further, comparative antibodies are measured similarly as above to obtain a mean. The negative control used was cells reacted with isotype control antibodies, and a mean was also obtained. Each mean fluorescence intensity value (mean) was used to calculate the number of molecules according to the protocol attached to the kit. As a result, the number of CAPRIN-1 molecules on the surface of various cancer cells recognized by the antibody #1 was $10^5$ or more per cell for all the examined human cancer cell lines. On the other hand, the number of molecules recognized by the comparative monoclonal antibodies 1 to 11 was less than $10^5$ per cell.

INDUSTRIAL APPLICABILITY

The antibody of the present invention is useful in the treatment and/or prevention of cancer.

All publications, patents, and patent applications cited herein are incorporated herein by reference in their entirety.

The invention claimed is:

1. An antibody or a fragment thereof which has immunological reactivity with a CAPRIN-1 protein, the antibody or the fragment thereof comprising a heavy chain variable region comprising complementarity determining regions of SEQ ID NOs: 5, 6, and 7 and a light chain variable region comprising complementarity determining regions of SEQ ID NOs: 9, 10, and 11.

2. The antibody or the fragment thereof according to claim 1, wherein the antibody is a human antibody, a humanized antibody, a chimeric antibody, a single-chain antibody, or a multispecific antibody.

3. The antibody or the fragment thereof according to claim 1, wherein the antibody or the fragment thereof is conjugated with an antitumor agent.

4. A pharmaceutical composition for treatment of CAPRIN-1-expressing cancer, comprising an antibody or a fragment thereof according to claim 1 as an active ingredient.

5. The pharmaceutical composition according to claim 4, wherein the cancer is breast cancer, kidney cancer, pancreatic cancer, large bowel cancer, lung cancer, brain tumor, gastric cancer, uterine cervix cancer, ovary cancer, prostate cancer, urinary bladder cancer, esophageal cancer, leukemia, lymphoma, fibrosarcoma, mastocytoma, or melanoma.

6. A pharmaceutical combination for treatment of CAPRIN-1-expressing cancer, comprising a pharmaceutical composition according to claim 4 or 5 and a pharmaceutical composition comprising an antitumor agent.

7. A DNA encoding an antibody or a fragment thereof according to claim 1.

8. A method for treating CAPRIN-1-expressing cancer, comprising administering an antibody or a fragment thereof according to claim 1.

9. The antibody or the fragment thereof according to claim 2, wherein the antibody or the fragment thereof is conjugated with an antitumor agent.

10. A pharmaceutical composition for treatment of CAPRIN-1-expressing cancer, comprising an antibody or a fragment thereof according to claim 2 as an active ingredient.

11. A pharmaceutical composition for treatment of CAPRIN-1-expressing cancer, comprising an antibody or a fragment thereof according to claim 3 as an active ingredient.

12. A pharmaceutical combination for treatment of CAPRIN-1-expressing cancer, comprising a pharmaceutical composition according to claim 5 and a pharmaceutical composition comprising an antitumor agent.

13. A DNA encoding an antibody or a fragment thereof according to claim 2.

14. A method for treating CAPRIN-1-expressing cancer, comprising administering an antibody or a fragment thereof according to claim 2 to a test subject.

15. A method for treating CAPRIN-1-expressing cancer, comprising administering an antibody or a fragment thereof according to claim 3 to a test subject.

16. A method for treating CAPRIN-1-expressing cancer, comprising administering a pharmaceutical composition according to claim 4 to a test subject.

17. A method for treating CAPRIN-1-expressing cancer, comprising administering a pharmaceutical composition according to claim 5 to a test subject.

18. A method for treating CAPRIN-1-expressing cancer, comprising administering a pharmaceutical combination according to claim 6 to a test subject.

* * * * *

SEQUENCE LISTING

```
<160> NUMBER OF SEQ ID NOS: 38

<210> SEQ ID NO 1
<211> LENGTH: 5562
<212> TYPE: DNA
<213> ORGANISM: Homo sapiens
<220> FEATURE:
<221> NAME/KEY: CDS
<222> LOCATION: (190)..(2319)
<223> OTHER INFORMATION:

<400> SEQUENCE: 1
cagagggctg ctggctggct aagtccctcc cgctcccggc tctcgcctca ctaggagcgg      60
ctctcggtgc agcgggacag ggcgaagcgg cctgcgccca cggagcgcgc gacactgccc     120
ggaagggacc gccaccctttg ccccctcagc tgcccactcg tgatttccag cggcctccgc    180 gcgcgcacg atg ccc tcg gcc acc agc cac agc ggg agc ggc agc aag tcg    231
          Met Pro Ser Ala Thr Ser His Ser Gly Ser Gly Ser Lys Ser
            1               5                  10 tcc gga ccg cca ccg ccg tcg ggt tcc tcc ggg agt gag gcg gcc gcg    279
Ser Gly Pro Pro Pro Pro Ser Gly Ser Ser Gly Ser Glu Ala Ala Ala
 15                  20                  25                  30 gga gcc ggg gcc gcc gcg ccg gct tct cag cac ccc gca acc ggc acc    327
Gly Ala Gly Ala Ala Ala Pro Ala Ser Gln His Pro Ala Thr Gly Thr
                 35                  40                  45
```

| | | |
|---|---|---|
| ggc gct gtc cag acc gag gcc atg aag cag att ctc ggg gtg atc gac<br>Gly Ala Val Gln Thr Glu Ala Met Lys Gln Ile Leu Gly Val Ile Asp<br>50          55          60 | | 375 |
| aag aaa ctt cgg aac ctg gag aag aaa aag ggt aag ctt gat gat tac<br>Lys Lys Leu Arg Asn Leu Glu Lys Lys Lys Gly Lys Leu Asp Asp Tyr<br>65          70          75 | | 423 |
| cag gaa cga atg aac aaa ggg gaa agg ctt aat caa gat cag ctg gat<br>Gln Glu Arg Met Asn Lys Gly Glu Arg Leu Asn Gln Asp Gln Leu Asp<br>80          85          90 | | 471 |
| gcc gtt tct aag tac cag gaa gtc aca aat aat ttg gag ttt gca aaa<br>Ala Val Ser Lys Tyr Gln Glu Val Thr Asn Asn Leu Glu Phe Ala Lys<br>95          100         105         110 | | 519 |
| gaa tta cag agg agt ttc atg gca cta agt caa gat att cag aaa aca<br>Glu Leu Gln Arg Ser Phe Met Ala Leu Ser Gln Asp Ile Gln Lys Thr<br>115         120         125 | | 567 |
| ata aag aag aca gca cgt cgg gag cag ctt atg aga gaa gaa gct gaa<br>Ile Lys Lys Thr Ala Arg Arg Glu Gln Leu Met Arg Glu Glu Ala Glu<br>130         135         140 | | 615 |
| cag aaa cgt tta aaa act gta ctt gag cta cag tat gtt ttg gac aaa<br>Gln Lys Arg Leu Lys Thr Val Leu Glu Leu Gln Tyr Val Leu Asp Lys<br>145         150         155 | | 663 |
| ttg gga gat gat gaa gtg cgg act gac ctg aaa caa ggt ttg aat gga<br>Leu Gly Asp Asp Glu Val Arg Thr Asp Leu Lys Gln Gly Leu Asn Gly<br>160         165         170 | | 711 |
| gtg cca ata ttg tcc gaa gag gag ttg tca ttg ttg gat gaa ttc tat<br>Val Pro Ile Leu Ser Glu Glu Glu Leu Ser Leu Leu Asp Glu Phe Tyr<br>175         180         185         190 | | 759 |
| aag cta gta gac cct gaa cgg gac atg agc ttg agg ttg aat gaa cag<br>Lys Leu Val Asp Pro Glu Arg Asp Met Ser Leu Arg Leu Asn Glu Gln<br>195         200         205 | | 807 |
| tat gaa cat gcc tcc att cac ctg tgg gac ctg ctg gaa ggg aag gaa<br>Tyr Glu His Ala Ser Ile His Leu Trp Asp Leu Leu Glu Gly Lys Glu<br>210         215         220 | | 855 |
| aaa cct gta tgt gga acc acc tat aaa gtt cta aag gaa att gtt gag<br>Lys Pro Val Cys Gly Thr Thr Tyr Lys Val Leu Lys Glu Ile Val Glu<br>225         230         235 | | 903 |
| cgt gtt ttt cag tca aac tac ttt gac agc acc cac aac cac cag aat<br>Arg Val Phe Gln Ser Asn Tyr Phe Asp Ser Thr His Asn His Gln Asn<br>240         245         250 | | 951 |
| ggg ctg tgt gag gaa gaa gag gca gcc tca gca cct gca gtt gaa gac<br>Gly Leu Cys Glu Glu Glu Glu Ala Ala Ser Ala Pro Ala Val Glu Asp<br>255         260         265         270 | | 999 |
| cag gta cct gaa gct gaa cct gag cca gca gaa gag tac act gag caa<br>Gln Val Pro Glu Ala Glu Pro Glu Pro Ala Glu Glu Tyr Thr Glu Gln<br>275         280         285 | | 1047 |
| agt gaa gtt gaa tca aca gag tat gta aat aga cag ttc atg gca gaa<br>Ser Glu Val Glu Ser Thr Glu Tyr Val Asn Arg Gln Phe Met Ala Glu<br>290         295         300 | | 1095 |
| aca cag ttc acc agt ggt gaa aag gag cag gta gat gag tgg aca gtt<br>Thr Gln Phe Thr Ser Gly Glu Lys Glu Gln Val Asp Glu Trp Thr Val<br>305         310         315 | | 1143 |
| gaa acg gtt gag gtg gta aat tca ctc cag cag caa cct cag gct gca<br>Glu Thr Val Glu Val Val Asn Ser Leu Gln Gln Gln Pro Gln Ala Ala<br>320         325         330 | | 1191 |
| tcc cct tca gta cca gag ccc cac tct ttg act cca gtg gct cag gca<br>Ser Pro Ser Val Pro Glu Pro His Ser Leu Thr Pro Val Ala Gln Ala<br>335         340         345         350 | | 1239 |
| gat ccc ctt gtg aga aga cag cga gta caa gac ctt atg gca caa atg<br>Asp Pro Leu Val Arg Arg Gln Arg Val Gln Asp Leu Met Ala Gln Met<br>355         360         365 | | 1287 |

| | |
|---|---|
| cag ggt ccc tat aat ttc ata cag gat tca atg ctg gat ttt gaa aat<br>Gln Gly Pro Tyr Asn Phe Ile Gln Asp Ser Met Leu Asp Phe Glu Asn<br>370                        375                     380 | 1335 |
| cag aca ctt gat cct gcc att gta tct gca cag cct atg aat cca aca<br>Gln Thr Leu Asp Pro Ala Ile Val Ser Ala Gln Pro Met Asn Pro Thr<br>       385                        390                        395 | 1383 |
| caa aac atg gac atg ccc cag ctg gtt tgc cct cca gtt cat tct gaa<br>Gln Asn Met Asp Met Pro Gln Leu Val Cys Pro Pro Val His Ser Glu<br>400                        405                        410 | 1431 |
| tct aga ctt gct cag cct aat caa gtt cct gta caa cca gaa gcg aca<br>Ser Arg Leu Ala Gln Pro Asn Gln Val Pro Val Gln Pro Glu Ala Thr<br>415                        420                        425                        430 | 1479 |
| cag gtt cct ttg gta tca tcc aca agt gag ggg tac aca gca tct caa<br>Gln Val Pro Leu Val Ser Ser Thr Ser Glu Gly Tyr Thr Ala Ser Gln<br>                       435                        440                        445 | 1527 |
| ccc ttg tac cag cct tct cat gct aca gag caa cga cca cag aag gaa<br>Pro Leu Tyr Gln Pro Ser His Ala Thr Glu Gln Arg Pro Gln Lys Glu<br>             450                        455                        460 | 1575 |
| cca att gat cag att cag gca aca atc tct tta aat aca gac cag act<br>Pro Ile Asp Gln Ile Gln Ala Thr Ile Ser Leu Asn Thr Asp Gln Thr<br>                       465                        470                        475 | 1623 |
| aca gca tca tca tcc ctt cct gct gcg tct cag cct caa gta ttt cag<br>Thr Ala Ser Ser Ser Leu Pro Ala Ala Ser Gln Pro Gln Val Phe Gln<br>480                        485                        490 | 1671 |
| gct ggg aca agc aaa cct tta cat agc agt gga atc aat gta aat gca<br>Ala Gly Thr Ser Lys Pro Leu His Ser Ser Gly Ile Asn Val Asn Ala<br>495                        500                        505                        510 | 1719 |
| gct cca ttc caa tcc atg caa acg gtg ttc aat atg aat gcc cca gtt<br>Ala Pro Phe Gln Ser Met Gln Thr Val Phe Asn Met Asn Ala Pro Val<br>                       515                        520                        525 | 1767 |
| cct cct gtt aat gaa cca gaa act tta aaa cag caa aat cag tac cag<br>Pro Pro Val Asn Glu Pro Glu Thr Leu Lys Gln Gln Asn Gln Tyr Gln<br>             530                        535                        540 | 1815 |
| gcc agt tat aac cag agc ttt tct agt cag cct cac caa gta gaa caa<br>Ala Ser Tyr Asn Gln Ser Phe Ser Ser Gln Pro His Gln Val Glu Gln<br>                       545                        550                        555 | 1863 |
| aca gag ctt cag caa gaa cag ctt caa aca gtg gtt ggc act tac cat<br>Thr Glu Leu Gln Gln Glu Gln Leu Gln Thr Val Val Gly Thr Tyr His<br>560                        565                        570 | 1911 |
| ggt tcc cca gac cag tcc cat caa gtg act ggt aac cac cag cag cct<br>Gly Ser Pro Asp Gln Ser His Gln Val Thr Gly Asn His Gln Gln Pro<br>575                        580                        585                        590 | 1959 |
| cct cag cag aac act gga ttt cca cgt agc aat cag ccc tat tac aat<br>Pro Gln Gln Asn Thr Gly Phe Pro Arg Ser Asn Gln Pro Tyr Tyr Asn<br>                       595                        600                        605 | 2007 |
| agt cgt ggt gtg tct cgt gga ggc tcc cgt ggt gct aga ggc ttg atg<br>Ser Arg Gly Val Ser Arg Gly Gly Ser Arg Gly Ala Arg Gly Leu Met<br>             610                        615                        620 | 2055 |
| aat gga tac cgg ggc cct gcc aat gga ttc aga gga gga tat gat ggt<br>Asn Gly Tyr Arg Gly Pro Ala Asn Gly Phe Arg Gly Gly Tyr Asp Gly<br>                       625                        630                        635 | 2103 |
| tac cgc cct tca ttc tct aac act cca aac agt ggt tat aca cag tct<br>Tyr Arg Pro Ser Phe Ser Asn Thr Pro Asn Ser Gly Tyr Thr Gln Ser<br>             640                        645                        650 | 2151 |
| cag ttc agt gct ccc cgg gat tac tct ggc tat caa cgg gat gga tat<br>Gln Phe Ser Ala Pro Arg Asp Tyr Ser Gly Tyr Gln Arg Asp Gly Tyr<br>655                        660                        665                        670 | 2199 |
| cag cag aat ttc aag cga ggc tct ggg cag agt gga cca cgg gga gcc<br>Gln Gln Asn Phe Lys Arg Gly Ser Gly Gln Ser Gly Pro Arg Gly Ala | 2247 |

|  |  |  | 675 |  |  |  | 680 |  |  |  | 685 |  |  |  |
|---|---|---|---|---|---|---|---|---|---|---|---|---|---|---|
| cca | cga | ggt | cgt | gga | ggg | ccc | cca | aga | ccc | aac | aga | ggg | atg | ccg | caa | 2295 |
| Pro | Arg | Gly | Arg | Gly | Gly | Pro | Pro | Arg | Pro | Asn | Arg | Gly | Met | Pro | Gln |  |
|  |  | 690 |  |  |  |  | 695 |  |  |  |  | 700 |  |  |  |  |

| atg | aac | act | cag | caa | gtg | aat | taa | tctgattcac aggattatgt ttaatcgcca | 2349 |
|---|---|---|---|---|---|---|---|---|---|
| Met | Asn | Thr | Gln | Gln | Val | Asn |  |  |  |
|  |  | 705 |  |  |  |  |  |  |  |

```
aaaacacact ggccagtgta ccataatatg ttaccagaag agttattatc tatttgttct    2409
ccctttcagg aaacttattg taaagggact gttttcatcc cataaagaca ggactacaat    2469
tgtcagcttt ctattacctg gatatggaag gaaactattt ttactctgca tgttctgtcc    2529
taagcgtcat cttgagcctt gcacatgata ctcagattcc tcacccttgc ttaggagtaa    2589
aacaatatac tttacagggt gataataatc tccatagtta tttgaagtgg cttgaaaaag    2649
gcaagattga cttttatgac attggataaa atctacaaat cagccctcga gttattcaat    2709
gataactgac aaactaaatt atttccctag aaaggaagat gaaaggagtg gagtgtggtt    2769
tggcagaaca actgcatttc acagcttttc cagttaaatt ggagcactga acgttcagat    2829
gcataccaaa ttatgcatgg gtcctaatca cacatataag gctggctacc agctttgaca    2889
cagcactgtt catctggcca aacaactgtg gttaaaaaca catgtaaaat gcttttttaac    2949
agctgatact gtataagaca aagccaagat gcaaaattag ctttgattg cacttttg      3009
aaaaatatgc aacaaatatg ggatgtaatc cggatggccg cttctgtact taatgtgaaa    3069
tatttagata ccttttttgaa cacttaacag tttctttgag acaatgactt ttgtaaggat    3129
tggtactatc tatcattcct tatgacatgt acattgtctg tcactaatcc ttggattttg    3189
ctgtattgtc acctaaattg gtacaggtac tgatgaaaat ctctagtgga taatcataac    3249
actctcggtc acatgttttt ccttcagctt gaaagctttt ttttaaaagg aaagatacc     3309
aaatgcctgc tgctaccacc ctttttcaatt gctatctttt gaaaggcacc agtatgtgtt   3369
ttagattgat ttccctgttt cagggaaatc acggacagta gtttcagttc tgatggtata   3429
agcaaaacaa ataaaacgtt tataaaagtt gtatcttgaa acactggtgt tcaacagcta   3489
gcagcttatg tgattcaccc catgccacgt tagtgtcaca aattttatgg tttatctcca   3549
gcaacatttc tctagtactt gcacttatta tcttttgtct aatttaaccct taactgaatt   3609
ctccgttttct cctggaggca tttatattca gtgataattc cttcccttag atgcataggg  3669
agagtctcta aatttgatgg aaatggacac ttgagtagtg acttagcctt atgtactctg   3729
ttggaattttg tgctagcagt ttgagcacta gttctgtgtg cctaggaagt taatgctgct  3789
tattgtctca ttctgacttc atggagaatt aatcccacct ttaagcaaag gctactaagt   3849
taatggtatt ttctgtgcag aaattaaatt ttatttttcag catttagccc aggaattctt  3909
ccagtaggtg ctcagctatt taaaaacaaa actattctca acattcatc attagacaac    3969
tggagttttt gctggttttg taacctacca aatggatag gctgttgaac attccacatt    4029
caaaagtttt gtagggtggt gggaaatggg ggatcttcaa tgtttatttt aaaataaaat   4089
aaaataagtt cttgactttt ctcatgtgtg gttgtggtac atcatattgg aagggttaac   4149
ctgttacttt ggcaaatgag tattttttttg ctagcacctc cccttgcgtg ctttaaatga  4209
catctgcctg ggatgtacca caaccatatg ttacctgtat cttaggggaa tggataaaat   4269
atttgtggtt tactgggtaa tccctagatg atgtatgctt gcagtccctat ataaaactaa  4329
atttgctatc tgtgtagaaa ataatttcat gacatttaca atcaggactg aagtaagttc   4389
ttcacacagt gacctctgaa tcagtttcag agaagggatg ggggagaaaa tgccttctag   4449
```

```
gttttgaact tctatgcatt agtgcagatg ttgtgaatgt gtaaaggtgt tcatagtttg    4509
actgtttcta tgtatgtttt ttcaaagaat tgttcctttt tttgaactat aattttttctt   4569 tttttggtta ttttaccatc acagtttaaa tgtatatctt ttatgtctct actcagacca   4629
tatttttaaa ggggtgcctc attatggggc agagaacttt tcaataagtc tcattaagat   4689
ctgaatcttg gttctaagca ttctgtataa tatgtgattg cttgtcctag ctgcagaagg   4749 cctttttgttt ggtcaaatgc atattttagc agagtttcaa ggaaatgatt gtcacacatg   4809
tcactgtagc ctcttggtgt agcaagctca catacaaaat acttttgtat atgcataata   4869
taaatcatct catgtggata tgaaacttct tttttaaaac ttaaaaggt agaatgttat    4929 tgattacctt gattagggca gttttatttc cagatcctaa taattcctaa aaaatatgga   4989
aaagtttttt ttcaatcatt gtaccttgat attaaaacaa atatcctta agtatttcta   5049 atcagttagc ttctacagtt cttttgtctc cttttatatg cagctcttac gtgggagact   5109
tttccactta aaggagacat agaatgtgtg cttattctca gaaggttcat taactgaggt   5169
gatgagttaa caactagttg agcagtcagc ttcctaagtg ttttaggaca tttgttcatt   5229
atattttccg tcatataact agaggaagtg gaatgcagat aagtgccgaa ttcaaaccct   5289
tcattttatg tttaagctcc tgaatctgca ttccacttgg gttgttttta agcattctaa   5349
attttagttg attataagtt agatttcaca gaatcagtat tgcccttgat cttgtccttt   5409
ttatggagtt aacggggagg aagacccctc aggaaaacga agtaaattg ttaaggctca   5469 tcttcatacc tttttccatt ttgaatccta caaaaatact gcaaaagact agtgaatgtt   5529
taaaattaca ctagattaaa taatatgaaa gtc                                 5562
```

<210> SEQ ID NO 2
<211> LENGTH: 709
<212> TYPE: PRT
<213> ORGANISM: Homo sapiens

<400> SEQUENCE: 2

```
Met Pro Ser Ala Thr Ser His Ser Gly Ser Gly Ser Lys Ser Gly
1               5                   10                  15

Pro Pro Pro Pro Ser Gly Ser Ser Gly Ser Glu Ala Ala Gly Ala
                20                  25                  30

Gly Ala Ala Ala Pro Ala Ser Gln His Pro Ala Thr Gly Thr Gly Ala
                35                  40                  45

Val Gln Thr Glu Ala Met Lys Gln Ile Leu Gly Val Ile Asp Lys Lys
        50                  55                  60

Leu Arg Asn Leu Glu Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
                100                 105                 110

Gln Arg Ser Phe Met Ala Leu Ser Gln Asp Ile Gln Lys Thr Ile Lys
                115                 120                 125

Lys Thr Ala Arg Arg Glu Gln Leu Met Arg Glu Ala Glu Gln Lys
                130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175
```

```
Ile Leu Ser Glu Glu Leu Ser Leu Leu Asp Glu Phe Tyr Lys Leu
            180                 185                 190

Val Asp Pro Glu Arg Asp Met Ser Leu Arg Leu Asn Glu Gln Tyr Glu
        195                 200                 205

His Ala Ser Ile His Leu Trp Asp Leu Leu Glu Gly Lys Glu Lys Pro
    210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Ala Ala Ser Ala Pro Ala Val Glu Asp Gln Val
            260                 265                 270

Pro Glu Ala Glu Pro Glu Pro Ala Glu Glu Tyr Thr Glu Gln Ser Glu
        275                 280                 285

Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
        355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
            405                 410                 415

Leu Ala Gln Pro Asn Gln Val Pro Val Gln Pro Glu Ala Thr Gln Val
        420                 425                 430

Pro Leu Val Ser Ser Thr Ser Glu Gly Tyr Thr Ala Ser Gln Pro Leu
    435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
            485                 490                 495

Thr Ser Lys Pro Leu His Ser Ser Gly Ile Asn Val Asn Ala Ala Pro
        500                 505                 510

Phe Gln Ser Met Gln Thr Val Phe Asn Met Asn Ala Pro Val Pro Pro
    515                 520                 525

Val Asn Glu Pro Glu Thr Leu Lys Gln Gln Asn Gln Tyr Gln Ala Ser
    530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
            565                 570                 575

Pro Asp Gln Ser His Gln Val Thr Gly Asn His Gln Gln Pro Pro Gln
        580                 585                 590
```

```
Gln Asn Thr Gly Phe Pro Arg Ser Asn Gln Pro Tyr Tyr Asn Ser Arg
            595                 600                 605

Gly Val Ser Arg Gly Ser Arg Gly Ala Arg Gly Leu Met Asn Gly
610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
            645                 650                 655

Ser Ala Pro Arg Asp Tyr Ser Gly Tyr Gln Arg Asp Gly Tyr Gln Gln
                660                 665                 670

Asn Phe Lys Arg Gly Ser Gly Gln Ser Gly Pro Arg Gly Ala Pro Arg
            675                 680                 685

Gly Arg Gly Gly Pro Pro Arg Pro Asn Arg Gly Met Pro Gln Met Asn
690                 695                 700

Thr Gln Gln Val Asn
705

<210> SEQ ID NO 3
<211> LENGTH: 3553
<212> TYPE: DNA
<213> ORGANISM: Homo sapiens
<220> FEATURE:
<221> NAME/KEY: CDS
<222> LOCATION: (190)..(2274)
<223> OTHER INFORMATION:

<400> SEQUENCE: 3
cagagggctg ctggctggct aagtccctcc cgctcccggc tctcgcctca ctaggagcgg      60
ctctcggtgc agcgggacag ggcgaagcgg cctgcgccca cggagcgcgc gacactgccc     120
ggaagggacc gccacccttg cccccctcagc tgcccactcg tgatttccag cggcctccgc   180 gcgcgcacg atg ccc tcg gcc acc agc cac agc ggg agc ggc agc aag tcg   231
          Met Pro Ser Ala Thr Ser His Ser Gly Ser Gly Ser Lys Ser
            1               5                   10 tcc gga ccg cca ccg ccg tcg ggt tcc tcc ggg agt gag gcg gcc gcg   279
Ser Gly Pro Pro Pro Pro Ser Gly Ser Ser Gly Ser Glu Ala Ala Ala
15                  20                  25                  30 gga gcc ggg gcc gcc gcg ccg gct tct cag cac ccc gca acc ggc acc   327
Gly Ala Gly Ala Ala Ala Pro Ala Ser Gln His Pro Ala Thr Gly Thr
                35                  40                  45 ggc gct gtc cag acc gag gcc atg aag cag att ctc ggg gtg atc gac   375
Gly Ala Val Gln Thr Glu Ala Met Lys Gln Ile Leu Gly Val Ile Asp
            50                  55                  60 aag aaa ctt cgg aac ctg gag aag aaa aag ggt aag ctt gat gat tac   423
Lys Lys Leu Arg Asn Leu Glu Lys Lys Lys Gly Lys Leu Asp Asp Tyr
65                  70                  75 cag gaa cga atg aac aaa ggg gaa agg ctt aat caa gat cag ctg gat   471
Gln Glu Arg Met Asn Lys Gly Glu Arg Leu Asn Gln Asp Gln Leu Asp
                80                  85                  90 gcc gtt tct aag tac cag gaa gtc aca aat aat ttg gag ttt gca aaa   519
Ala Val Ser Lys Tyr Gln Glu Val Thr Asn Asn Leu Glu Phe Ala Lys
95                  100                 105                 110 gaa tta cag agg agt ttc atg gca cta agt caa gat att cag aaa aca   567
Glu Leu Gln Arg Ser Phe Met Ala Leu Ser Gln Asp Ile Gln Lys Thr
                115                 120                 125 ata aag aag aca gca cgt cgg gag cag ctt atg aga gaa gaa gct gaa   615
Ile Lys Lys Thr Ala Arg Arg Glu Gln Leu Met Arg Glu Glu Ala Glu
            130                 135                 140 cag aaa cgt tta aaa act gta ctt gag cta cag tat gtt ttg gac aaa   663
```

```
             Gln Lys Arg Leu Lys Thr Val Leu Glu Leu Gln Tyr Val Leu Asp Lys
                         145                 150                 155 ttg gga gat gat gaa gtg cgg act gac ctg aaa caa ggt ttg aat gga        711
Leu Gly Asp Asp Glu Val Arg Thr Asp Leu Lys Gln Gly Leu Asn Gly
        160                 165                 170 gtg cca ata ttg tcc gaa gag gag ttg tca ttg ttg gat gaa ttc tat        759
Val Pro Ile Leu Ser Glu Glu Glu Leu Ser Leu Leu Asp Glu Phe Tyr
175                 180                 185                 190 aag cta gta gac cct gaa cgg gac atg agc ttg agg ttg aat gaa cag        807
Lys Leu Val Asp Pro Glu Arg Asp Met Ser Leu Arg Leu Asn Glu Gln
                    195                 200                 205 tat gaa cat gcc tcc att cac ctg tgg gac ctg ctg gaa ggg aag gaa        855
Tyr Glu His Ala Ser Ile His Leu Trp Asp Leu Leu Glu Gly Lys Glu
            210                 215                 220 aaa cct gta tgt gga acc acc tat aaa gtt cta aag gaa att gtt gag        903
Lys Pro Val Cys Gly Thr Thr Tyr Lys Val Leu Lys Glu Ile Val Glu
                225                 230                 235 cgt gtt ttt cag tca aac tac ttt gac agc acc cac aac cac cag aat        951
Arg Val Phe Gln Ser Asn Tyr Phe Asp Ser Thr His Asn His Gln Asn
240                 245                 250 ggg ctg tgt gag gaa gaa gag gca gcc tca gca cct gca gtt gaa gac        999
Gly Leu Cys Glu Glu Glu Glu Ala Ala Ser Ala Pro Ala Val Glu Asp
255                 260                 265                 270 cag gta cct gaa gct gaa cct gag cca gca gaa gag tac act gag caa       1047
Gln Val Pro Glu Ala Glu Pro Glu Pro Ala Glu Glu Tyr Thr Glu Gln
                    275                 280                 285 agt gaa gtt gaa tca aca gag tat gta aat aga cag ttc atg gca gaa       1095
Ser Glu Val Glu Ser Thr Glu Tyr Val Asn Arg Gln Phe Met Ala Glu
            290                 295                 300 aca cag ttc acc agt ggt gaa aag gag cag gta gat gag tgg aca gtt       1143
Thr Gln Phe Thr Ser Gly Glu Lys Glu Gln Val Asp Glu Trp Thr Val
                305                 310                 315 gaa acg gtt gag gtg gta aat tca ctc cag cag caa cct cag gct gca       1191
Glu Thr Val Glu Val Val Asn Ser Leu Gln Gln Gln Pro Gln Ala Ala
320                 325                 330 tcc cct tca gta cca gag ccc cac tct ttg act cca gtg gct cag gca       1239
Ser Pro Ser Val Pro Glu Pro His Ser Leu Thr Pro Val Ala Gln Ala
335                 340                 345                 350 gat ccc ctt gtg aga aga cag cga gta caa gac ctt atg gca caa atg       1287
Asp Pro Leu Val Arg Arg Gln Arg Val Gln Asp Leu Met Ala Gln Met
                    355                 360                 365 cag ggt ccc tat aat ttc ata cag gat tca atg ctg gat ttt gaa aat       1335
Gln Gly Pro Tyr Asn Phe Ile Gln Asp Ser Met Leu Asp Phe Glu Asn
            370                 375                 380 cag aca ctt gat cct gcc att gta tct gca cag cct atg aat cca aca       1383
Gln Thr Leu Asp Pro Ala Ile Val Ser Ala Gln Pro Met Asn Pro Thr
                385                 390                 395 caa aac atg gac atg ccc cag ctg gtt tgc cct cca gtt cat tct gaa       1431
Gln Asn Met Asp Met Pro Gln Leu Val Cys Pro Pro Val His Ser Glu
400                 405                 410 tct aga ctt gct cag cct aat caa gtt cct gta caa cca gaa gcg aca       1479
Ser Arg Leu Ala Gln Pro Asn Gln Val Pro Val Gln Pro Glu Ala Thr
415                 420                 425                 430 cag gtt cct ttg gta tca tcc aca agt gag ggg tac aca gca tct caa       1527
Gln Val Pro Leu Val Ser Ser Thr Ser Glu Gly Tyr Thr Ala Ser Gln
                    435                 440                 445 ccc ttg tac cag cct tct cat gct aca gag caa cga cca cag aag gaa       1575
Pro Leu Tyr Gln Pro Ser His Ala Thr Glu Gln Arg Pro Gln Lys Glu
            450                 455                 460
```

-continued

```
cca att gat cag att cag gca aca atc tct tta aat aca gac cag act    1623
Pro Ile Asp Gln Ile Gln Ala Thr Ile Ser Leu Asn Thr Asp Gln Thr
        465                 470                 475 aca gca tca tca tcc ctt cct gct gcg tct cag cct caa gta ttt cag    1671
Thr Ala Ser Ser Ser Leu Pro Ala Ala Ser Gln Pro Gln Val Phe Gln
    480                 485                 490 gct ggg aca agc aaa cct tta cat agc agt gga atc aat gta aat gca    1719
Ala Gly Thr Ser Lys Pro Leu His Ser Ser Gly Ile Asn Val Asn Ala
495                 500                 505                 510 gct cca ttc caa tcc atg caa acg gtg ttc aat atg aat gcc cca gtt    1767
Ala Pro Phe Gln Ser Met Gln Thr Val Phe Asn Met Asn Ala Pro Val
            515                 520                 525 cct cct gtt aat gaa cca gaa act tta aaa cag caa aat cag tac cag    1815
Pro Pro Val Asn Glu Pro Glu Thr Leu Lys Gln Gln Asn Gln Tyr Gln
        530                 535                 540 gcc agt tat aac cag agc ttt tct agt cag cct cac caa gta gaa caa    1863
Ala Ser Tyr Asn Gln Ser Phe Ser Ser Gln Pro His Gln Val Glu Gln
    545                 550                 555 aca gag ctt cag caa gaa cag ctt caa aca gtg gtt ggc act tac cat    1911
Thr Glu Leu Gln Gln Glu Gln Leu Gln Thr Val Val Gly Thr Tyr His
560                 565                 570 ggt tcc cca gac cag tcc cat caa gtg act ggt aac cac cag cag cct    1959
Gly Ser Pro Asp Gln Ser His Gln Val Thr Gly Asn His Gln Gln Pro
575                 580                 585                 590 cct cag cag aac act gga ttt cca cgt agc aat cag ccc tat tac aat    2007
Pro Gln Gln Asn Thr Gly Phe Pro Arg Ser Asn Gln Pro Tyr Tyr Asn
            595                 600                 605 agt cgt ggt gtg tct cgt gga ggc tcc cgt ggt gct aga ggc ttg atg    2055
Ser Arg Gly Val Ser Arg Gly Gly Ser Arg Gly Ala Arg Gly Leu Met
        610                 615                 620 aat gga tac cgg ggc cct gcc aat gga ttc aga gga gga tat gat ggt    2103
Asn Gly Tyr Arg Gly Pro Ala Asn Gly Phe Arg Gly Gly Tyr Asp Gly
    625                 630                 635 tac cgc cct tca ttc tct aac act cca aac agt ggt tat aca cag tct    2151
Tyr Arg Pro Ser Phe Ser Asn Thr Pro Asn Ser Gly Tyr Thr Gln Ser
640                 645                 650 cag ttc agt gct ccc cgg gat tac tct ggc tat caa cgg gat gga tat    2199
Gln Phe Ser Ala Pro Arg Asp Tyr Ser Gly Tyr Gln Arg Asp Gly Tyr
655                 660                 665                 670 cag cag aat ttc aag cga ggc tct ggg cag agt gga cca cgg gga gcc    2247
Gln Gln Asn Phe Lys Arg Gly Ser Gly Gln Ser Gly Pro Arg Gly Ala
            675                 680                 685 cca cga ggt aat att ttg tgg tgg tga tcctagctcc taagtggagc         2294
Pro Arg Gly Asn Ile Leu Trp Trp
        690 ttctgttctg gccttggaag agctgttaat agtctgcatg ttaggaatac atttatcctt  2354 tccagacttg ttgctaggga ttaaatgaaa tgctctgttt ctaaaactta atcttggacc  2414 caaattttaa tttttgaatg atttaatttt ccctgttact atataaactg tcttgaaaac  2474 tagaacatat tctcttctca gaaaaagtgt ttttccaact gaaaattatt tttcaggtcc  2534 taaaacctgc taaatgtttt taggaagtac ttactgaaac attttgtaa gacattttg    2594 gaatgagatt gaacatttat ataaatttat tattcctctt tcattttttt gaaacatgcc  2654 tattatattt tagggccaga cacccttta tggccggata agccatagtt aacatttaga   2714 gaaccatta gaagtgatag aactaatgga atttgcaatg ccttttggac ctctattagt   2774 gatataaata tcaagttatt tctgactttt aaacaaaact cccaaattcc taacttattg  2834 agctatactt aaaaaaaatt acaggtttag agagtttttt gttttctttt tactgttgga  2894
```

```
aaactacttc ccattttggc aggaagttaa cctatttaac aattagagct agcatttcat    2954
gtagtctgaa attctaaatg gttctctgat ttgagggagg ttaaacatca aacaggtttc    3014
ctctattggc cataacatgt ataaaatgtg tgttaaggag gaattacaac gtactttgat    3074
ttgaatacta gtagaaactg gccaggaaaa aggtacattt ttctaaaaat taatggatca    3134
cttgggaatt actgacttga ctagaagtat caaaggatgt ttgcatgtga atgtgggtta    3194
tgttctttcc cacctgtag catattcgat gaaagttgag ttaactgata gctaaaaatc    3254
tgttttaaca gcatgtaaaa agttatttta tctgttaaaa gtcattatac agttttgaat    3314
gttatgtagt ttcttttaa cagtttaggt aataaggtct gttttcattc tggtgctttt    3374
attaattttg atagtatgat gttacttact actgaaatgt aagctagagt gtacactaga    3434
atgtaagctc catgagagca ggtaccttgt ctgtcttctc tgctgtatct attcccaacg    3494
cttgatgatg gtgcctggca catagtaggc actcaataaa tatttgttga atgaatgaa    3553
```

<210> SEQ ID NO 4
<211> LENGTH: 694
<212> TYPE: PRT
<213> ORGANISM: Homo sapiens

<400> SEQUENCE: 4

```
Met Pro Ser Ala Thr Ser His Ser Gly Ser Gly Ser Lys Ser Gly
1               5                   10                  15

Pro Pro Pro Pro Ser Gly Ser Ser Gly Ser Glu Ala Ala Gly Ala
                20                  25                  30

Gly Ala Ala Ala Pro Ala Ser Gln His Pro Ala Thr Gly Thr Gly Ala
                35                  40                  45

Val Gln Thr Glu Ala Met Lys Gln Ile Leu Gly Val Ile Asp Lys Lys
50                  55                  60

Leu Arg Asn Leu Glu Lys Lys Gly Lys Leu Asp Asp Tyr Gln Glu
65                  70                  75                  80

Arg Met Asn Lys Gly Glu Arg Leu Asn Gln Asp Leu Asp Ala Val
                85                  90                  95

Ser Lys Tyr Gln Glu Val Thr Asn Asn Leu Glu Phe Ala Lys Glu Leu
                100                 105                 110

Gln Arg Ser Phe Met Ala Leu Ser Gln Asp Ile Gln Lys Thr Ile Lys
            115                 120                 125

Lys Thr Ala Arg Arg Glu Gln Leu Met Arg Glu Glu Ala Glu Gln Lys
        130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Leu Ser Leu Leu Asp Glu Phe Tyr Lys Leu
                180                 185                 190

Val Asp Pro Glu Arg Asp Met Ser Leu Arg Leu Asn Glu Gln Tyr Glu
            195                 200                 205

His Ala Ser Ile His Leu Trp Asp Leu Leu Glu Gly Lys Glu Lys Pro
        210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255
```

```
Cys Glu Glu Glu Ala Ala Ser Ala Pro Ala Val Glu Asp Gln Val
            260                 265                 270
Pro Glu Ala Glu Pro Glu Pro Ala Glu Glu Tyr Thr Glu Gln Ser Glu
        275                 280                 285
Val Glu Ser Thr Glu Tyr Val Asn Arg Gln Phe Met Ala Glu Thr Gln
    290                 295                 300
Phe Thr Ser Gly Glu Lys Glu Gln Val Asp Glu Trp Thr Val Glu Thr
305                 310                 315                 320
Val Glu Val Val Asn Ser Leu Gln Gln Gln Pro Gln Ala Ala Ser Pro
                325                 330                 335
Ser Val Pro Glu Pro His Ser Leu Thr Pro Val Ala Gln Ala Asp Pro
            340                 345                 350
Leu Val Arg Arg Gln Arg Val Gln Asp Leu Met Ala Gln Met Gln Gly
        355                 360                 365
Pro Tyr Asn Phe Ile Gln Asp Ser Met Leu Asp Phe Glu Asn Gln Thr
    370                 375                 380
Leu Asp Pro Ala Ile Val Ser Ala Gln Pro Met Asn Pro Thr Gln Asn
385                 390                 395                 400
Met Asp Met Pro Gln Leu Val Cys Pro Pro Val His Ser Glu Ser Arg
                405                 410                 415
Leu Ala Gln Pro Asn Gln Val Pro Val Gln Pro Glu Ala Thr Gln Val
            420                 425                 430
Pro Leu Val Ser Ser Thr Ser Glu Gly Tyr Thr Ala Ser Gln Pro Leu
        435                 440                 445
Tyr Gln Pro Ser His Ala Thr Glu Gln Arg Pro Gln Lys Glu Pro Ile
    450                 455                 460
Asp Gln Ile Gln Ala Thr Ile Ser Leu Asn Thr Asp Gln Thr Thr Ala
465                 470                 475                 480
Ser Ser Ser Leu Pro Ala Ala Ser Gln Pro Gln Val Phe Gln Ala Gly
                485                 490                 495
Thr Ser Lys Pro Leu His Ser Ser Gly Ile Asn Val Asn Ala Ala Pro
            500                 505                 510
Phe Gln Ser Met Gln Thr Val Phe Asn Met Asn Ala Pro Val Pro Pro
        515                 520                 525
Val Asn Glu Pro Glu Thr Leu Lys Gln Gln Asn Gln Tyr Gln Ala Ser
    530                 535                 540
Tyr Asn Gln Ser Phe Ser Ser Gln Pro His Gln Val Glu Gln Thr Glu
545                 550                 555                 560
Leu Gln Gln Glu Gln Leu Gln Thr Val Val Gly Thr Tyr His Gly Ser
                565                 570                 575
Pro Asp Gln Ser His Gln Val Thr Gly Asn His Gln Pro Pro Gln
            580                 585                 590
Gln Asn Thr Gly Phe Pro Arg Ser Asn Gln Pro Tyr Tyr Asn Ser Arg
        595                 600                 605
Gly Val Ser Arg Gly Gly Ser Arg Gly Ala Arg Gly Leu Met Asn Gly
    610                 615                 620
Tyr Arg Gly Pro Ala Asn Gly Phe Arg Gly Gly Tyr Asp Gly Tyr Arg
625                 630                 635                 640
Pro Ser Phe Ser Asn Thr Pro Asn Ser Gly Tyr Thr Gln Ser Gln Phe
                645                 650                 655
Ser Ala Pro Arg Asp Tyr Ser Gly Tyr Gln Arg Asp Gly Tyr Gln Gln
            660                 665                 670
Asn Phe Lys Arg Gly Ser Gly Gln Ser Gly Pro Arg Gly Ala Pro Arg
```

```
            675                 680                 685

Gly Asn Ile Leu Trp Trp
    690

<210> SEQ ID NO 5
<211> LENGTH: 5
<212> TYPE: PRT
<213> ORGANISM: Mus musculus

<400> SEQUENCE: 5

Ala Tyr Tyr Met His
1               5

<210> SEQ ID NO 6
<211> LENGTH: 17
<212> TYPE: PRT
<213> ORGANISM: Mus musculus

<400> SEQUENCE: 6

Arg Val Asn Pro Asn Asn Gly Gly Thr Thr Tyr Asn Gln Lys Phe Lys
1               5                   10                  15

Gly

<210> SEQ ID NO 7
<211> LENGTH: 11
<212> TYPE: PRT
<213> ORGANISM: Mus musculus

<400> SEQUENCE: 7

Arg Ile Tyr Tyr Gly Tyr Phe Asp Tyr Trp Gly
1               5                   10

<210> SEQ ID NO 8
<211> LENGTH: 111
<212> TYPE: PRT
<213> ORGANISM: Mus musculus

<400> SEQUENCE: 8

Gly Pro Asp Leu Val Lys Pro Gly Ala Ser Val Lys Ile Ser Cys Lys
1               5                   10                  15

Ala Ser Gly Tyr Ser Phe Thr Ala Tyr Tyr Met His Trp Val Lys Gln
                20                  25                  30

Ser His Gly Lys Ser Leu Glu Trp Ile Gly Arg Val Asn Pro Asn Asn
            35                  40                  45

Gly Gly Thr Thr Tyr Asn Gln Lys Phe Lys Gly Lys Ala Ile Leu Thr
        50                  55                  60

Val Asp Lys Ser Ser Ser Thr Ala Tyr Met Glu Leu Arg Ser Leu Thr
65                  70                  75                  80

Phe Glu Asp Ser Ala Val Tyr Tyr Cys Ala Arg Arg Ile Tyr Tyr Gly
                85                  90                  95

Tyr Phe Asp Tyr Trp Gly Gln Gly Thr Thr Val Thr Val Ser Ser
                100                 105                 110

<210> SEQ ID NO 9
<211> LENGTH: 15
<212> TYPE: PRT
<213> ORGANISM: Mus musculus

<400> SEQUENCE: 9

Lys Ala Ser Gln Ser Val Asp Tyr Asp Gly Asp Ser Tyr Met Asn
1               5                   10                  15
```

<210> SEQ ID NO 10
<211> LENGTH: 7
<212> TYPE: PRT
<213> ORGANISM: Mus musculus

<400> SEQUENCE: 10

Val Ala Ser Asn Leu Glu Ser
1               5

<210> SEQ ID NO 11
<211> LENGTH: 9
<212> TYPE: PRT
<213> ORGANISM: Mus musculus

<400> SEQUENCE: 11

Gln Gln Ser Asn Glu Asp Pro Tyr Thr
1               5

<210> SEQ ID NO 12
<211> LENGTH: 104
<212> TYPE: PRT
<213> ORGANISM: Mus musculus

<400> SEQUENCE: 12

Ala Phe Phe Ala Val Ser Leu Gly Gln Arg Ala Thr Ile Ser Cys Lys
1               5                   10                  15

Ala Ser Gln Ser Val Asp Tyr Asp Gly Asp Ser Tyr Met Asn Trp Tyr
                20                  25                  30

Gln Gln Lys Pro Gly Gln Pro Pro Lys Leu Leu Ile Tyr Val Ala Ser
            35                  40                  45

Asn Leu Glu Ser Gly Val Pro Ala Arg Phe Ser Gly Ser Gly Ser Gly
        50                  55                  60

Thr Asp Phe Thr Leu Asn Ile His Pro Val Glu Glu Asp Ala Ala
65                  70                  75                  80

Thr Tyr Tyr Cys Gln Gln Ser Asn Glu Asp Pro Tyr Thr Phe Gly Gly
                85                  90                  95

Gly Thr Lys Leu Glu Ile Lys Gln
            100

<210> SEQ ID NO 13
<211> LENGTH: 333
<212> TYPE: DNA
<213> ORGANISM: Mus musculus

<400> SEQUENCE: 13
ggacctgacc tggtgaagcc tggggcttca gtgaagatat cctgcaaggc ttctggttac    60
tcattcactg cctactacat gcactgggtg aagcagagcc atggaaagag ccttgagtgg   120
attggacgtg ttaatcctaa caatggtggt actacctaca accagaagtt caagggcaag   180
gccatattaa ctgtagataa gtcatccagc acagcctaca tggagctccg cagcctgaca   240
tttgaggact ctgcggtcta ttactgtgca agaaggattt actacggcta ctttgactac   300
tggggccaag ggaccacggt caccgtctcc tca                                333

<210> SEQ ID NO 14
<211> LENGTH: 312
<212> TYPE: DNA
<213> ORGANISM: Mus musculus

<400> SEQUENCE: 14

```
gcattctttg ctgtgtctct agggcagagg gccaccatct cctgcaaggc cagccaaagt      60
gttgattatg atggtgatag ttatatgaac tggtaccaac agaaaccagg acagccaccc     120
aaactcctca tctatgttgc atccaatctt gaatctgggg tcccagccag gttcagtggc     180
agtgggtctg ggacagactt caccctcaac atccatcctg tggaggagga ggatgctgca     240
acctattact gtcagcaaag taatgaggat ccgtacacgt tcggaggagg taccaagcta     300
gagatcaaac aa                                                        312
```

<210> SEQ ID NO 15
<211> LENGTH: 148
<212> TYPE: PRT
<213> ORGANISM: Mus musculus

<400> SEQUENCE: 15

```
Met Glu Trp Ser Gly Val Phe Ile Phe Leu Leu Ser Gly Thr Ala Gly
1               5                   10                  15

Val Leu Ser Glu Val Gln Leu His Gln Phe Gly Ala Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Asp Ser Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Ser Arg Ser Tyr Asp Tyr Glu Gly Phe Ala Tyr
        115                 120                 125

Trp Gly Gln Gly Thr Leu Val Thr Val Ser Ala Ala Lys Thr Thr Pro
    130                 135                 140

Pro Ser Val Tyr
145
```

<210> SEQ ID NO 16
<211> LENGTH: 139
<212> TYPE: PRT
<213> ORGANISM: Mus musculus

<400> SEQUENCE: 16

```
Met Ser Val Leu Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Gly Asn
        35                  40                  45

Ile His Asn Tyr Leu Ala Trp Tyr Gln Gln Lys Gln Gly Lys Ser Pro
    50                  55                  60

Gln Leu Leu Val Tyr Asn Ala Lys Thr Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Ser Tyr Tyr Cys Gln His Phe Trp
            100                 105                 110
```

```
Ser Thr Leu Thr Phe Gly Ala Gly Thr Lys Leu Glu Leu Lys Arg Ala
        115                 120                 125

Asp Ala Ala Pro Thr Val Ser Asn Pro Tyr Asp
        130                 135

<210> SEQ ID NO 17
<211> LENGTH: 148
<212> TYPE: PRT
<213> ORGANISM: Mus musculus

<400> SEQUENCE: 17

Met Glu Trp Ser Gly Val Phe Ile Phe Leu Leu Ser Gly Thr Ala Gly
1               5                   10                  15

Val Leu Ser Glu Val Gln Leu His Gln Phe Gly Ala Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Asp Ser Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Ser Arg Ser Tyr Asp Tyr Glu Gly Phe Ala Tyr
        115                 120                 125

Trp Gly Gln Gly Thr Leu Val Thr Val Ser Ala Ala Lys Thr Thr Pro
    130                 135                 140

Pro Ser Val Tyr
145

<210> SEQ ID NO 18
<211> LENGTH: 132
<212> TYPE: PRT
<213> ORGANISM: Mus musculus

<400> SEQUENCE: 18

Ala Val Leu Arg Cys Ser Arg Gly Leu Leu Val Ile Trp Ile Ser Asp
1               5                   10                  15

Ile Gln Leu Thr Gln Ser Pro Ser Ser Leu Ala Val Thr Ala Gly Glu
            20                  25                  30

Lys Val Thr Met Ser Cys Lys Ser Ser Gln Ser Leu Leu Trp Ser Val
            35                  40                  45

Asn Gln Lys Asn Tyr Leu Ser Trp Tyr Gln Gln Lys Gln Arg Gln Pro
        50                  55                  60

Pro Lys Leu Leu Ile Tyr Gly Ala Ser Ile Arg Glu Ser Trp Val Pro
65                  70                  75                  80

Asp Arg Phe Thr Gly Ser Gly Ser Gly Thr Asp Phe Thr Leu Thr Ile
                85                  90                  95

Ser Asn Val His Ala Glu Asp Leu Ala Val Tyr Tyr Cys Gln His Asn
            100                 105                 110

His Gly Ser Phe Leu Pro Ser Arg Ser Glu Gln Val Pro Ser Trp Arg
        115                 120                 125

Ser Asn Asn Arg
        130
```

<210> SEQ ID NO 19
<211> LENGTH: 148
<212> TYPE: PRT
<213> ORGANISM: Mus musculus

<400> SEQUENCE: 19

Met Glu Trp Ser Gly Val Phe Ile Phe Leu Leu Ser Gly Thr Ala Gly
1               5                   10                  15

Val Leu Ser Glu Val Gln Leu His Gln Phe Gly Ala Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Asp Ser Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Ser Arg Ser Tyr Asp Tyr Glu Gly Phe Ala Tyr
        115                 120                 125

Trp Gly Gln Gly Thr Leu Val Thr Val Ser Ala Ala Lys Thr Thr Pro
    130                 135                 140

Pro Ser Val Tyr
145

<210> SEQ ID NO 20
<211> LENGTH: 117
<212> TYPE: PRT
<213> ORGANISM: Mus musculus

<400> SEQUENCE: 20

Arg Thr Thr Ser His Met Asp Ser Asp Ile Gln Leu Thr Gln Ser Pro
1               5                   10                  15

Ala Ser Leu Ser Ala Ser Val Gly Glu Thr Val Thr Ile Thr Cys Arg
            20                  25                  30

Ala Ser Gly Asn Ile His Asn Tyr Leu Ala Trp Tyr Gln Gln Lys Gln
        35                  40                  45

Gly Lys Ser Pro Gln Leu Leu Val Tyr Asn Ala Lys Thr Leu Ala Asp
    50                  55                  60

Gly Val Pro Ser Arg Phe Ser Gly Ser Gly Ser Gly Thr Gln Tyr Ser
65                  70                  75                  80

Leu Lys Ile Asn Ser Leu Gln Pro Glu Asp Phe Gly Ser Tyr Tyr Cys
                85                  90                  95

Gln His Phe Trp Ser Thr Leu Thr Phe Gly Gly Gly Thr Lys Leu Glu
            100                 105                 110

Ile Lys Gln Ser Asp
        115

<210> SEQ ID NO 21
<211> LENGTH: 148
<212> TYPE: PRT
<213> ORGANISM: Mus musculus

<400> SEQUENCE: 21

```
Met Glu Trp Ser Gly Val Phe Ile Phe Leu Ser Gly Thr Ala Gly
1               5                   10                  15

Val Leu Ser Glu Val Gln Leu His Gln Phe Gly Ala Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Asp Ser Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Ser Arg Ser Tyr Asp Tyr Glu Gly Phe Ala Tyr
        115                 120                 125

Trp Gly Gln Gly Thr Leu Val Thr Val Ser Ala Ala Lys Thr Thr Pro
    130                 135                 140

Pro Ser Val Tyr
145

<210> SEQ ID NO 22
<211> LENGTH: 94
<212> TYPE: PRT
<213> ORGANISM: Mus musculus

<400> SEQUENCE: 22

Ser Gly Asp Arg Val Ser Leu Ser Cys Arg Ala Ser Gln Ser Ile Ser
1               5                   10                  15

Asn Tyr Leu His Trp Tyr Gln Gln Lys Ser His Glu Ser Pro Arg Leu
            20                  25                  30

Leu Ile Lys Tyr Ala Ser Gln Ser Ile Ser Gly Ile Pro Ser Arg Phe
        35                  40                  45

Ser Gly Ser Gly Ser Gly Thr Asp Phe Thr Leu Ser Ile Asn Ser Val
    50                  55                  60

Glu Thr Glu Asp Phe Gly Met Tyr Phe Cys Gln Gln Ser Asn Ser Trp
65                  70                  75                  80

Pro Tyr Thr Phe Gly Ala Gly Thr Lys Leu Glu Ile Lys Gln
                85                  90

<210> SEQ ID NO 23
<211> LENGTH: 148
<212> TYPE: PRT
<213> ORGANISM: Mus musculus

<400> SEQUENCE: 23

Met Glu Trp Ser Gly Val Phe Ile Phe Leu Ser Gly Thr Ala Gly
1               5                   10                  15

Val Leu Ser Glu Val Gln Leu His Gln Phe Gly Ala Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Asp Ser Thr Ser Tyr Asn
65                  70                  75                  80
```

```
Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Ser Arg Ser Tyr Asp Tyr Glu Gly Phe Ala Tyr
        115                 120                 125

Trp Gly Gln Gly Thr Leu Val Thr Val Ser Ala Ala Lys Thr Thr Pro
    130                 135                 140

Pro Ser Val Tyr
145

<210> SEQ ID NO 24
<211> LENGTH: 105
<212> TYPE: PRT
<213> ORGANISM: Mus musculus

<400> SEQUENCE: 24

Gly Leu Phe Cys Ser Val Glu Arg Cys His Tyr Gln Leu Gln Ser Ser
1               5                   10                  15

Gln Asn Leu Leu Ser Ile Val Asn Arg Tyr His Tyr Met Ser Gly Asn
            20                  25                  30

Pro Pro Lys Leu Leu Val Tyr Pro Ala Leu Leu Ile Tyr Glu Ala Ser
        35                  40                  45

Ile Thr Lys Ser Cys Val Pro Asp Arg Phe Thr Arg Ser Gly Ser Gly
    50                  55                  60

Thr Asn Phe Thr Leu Thr Ile Asn Phe Val His Ala Asp Asp Leu Ile
65                  70                  75                  80

Phe Tyr Tyr Cys Gln His Asn Arg Gly Ser Phe Leu Pro Ser Ser Ser
                85                  90                  95

Val Gln Val Pro Arg Arg Ser Asn
            100                 105

<210> SEQ ID NO 25
<211> LENGTH: 100
<212> TYPE: PRT
<213> ORGANISM: Mus musculus

<400> SEQUENCE: 25

Asp Ile Leu Gln Ala Ser Gly Tyr Ser Phe Thr Gly Tyr Thr Met Asn
1               5                   10                  15

Trp Val Lys Gln Ser His Gly Lys Asn Leu Glu Trp Ile Gly Leu Ile
            20                  25                  30

Asn Pro Tyr Asn Gly Gly Thr Ser Tyr Asn Gln Lys Phe Lys Gly Lys
        35                  40                  45

Ala Thr Leu Thr Val Asp Lys Ser Ser Ser Thr Ala Tyr Met Glu Leu
    50                  55                  60

Leu Ser Leu Thr Ser Glu Asp Ser Ala Val Tyr Tyr Cys Ala Arg Trp
65                  70                  75                  80

Gly Val Trp Ser Ala Met Asp Tyr Trp Gly Gln Gly Thr Thr Val Thr
                85                  90                  95

Val Ser Ser Lys
            100

<210> SEQ ID NO 26
<211> LENGTH: 90
<212> TYPE: PRT
<213> ORGANISM: Mus musculus
```

<400> SEQUENCE: 26

Asp Arg Val Ser Ile Thr Cys Lys Ala Ser Gln Asn Val Arg Thr Ala
1               5                   10                  15

Val Ala Trp Tyr Gln Gln Lys Pro Arg Gln Ser Pro Lys Ala Leu Ile
            20                  25                  30

Tyr Leu Ala Ser Asn Arg Asp Thr Gly Leu Pro Asp Arg Phe Pro Gly
        35                  40                  45

Arg Gly Ser Gly Thr Asp Phe Thr Leu Asn Ile Thr Asn Val Gln Ser
    50                  55                  60

Glu Asp Leu Glu Asp Tyr Phe Cys Leu Gln His Cys Asn Tyr Pro Asn
65                  70                  75                  80

Glu Phe Arg Gly Cys Thr Lys Val Pro Ile
                85                  90

<210> SEQ ID NO 27
<211> LENGTH: 116
<212> TYPE: PRT
<213> ORGANISM: Mus musculus

<400> SEQUENCE: 27

Leu Gln Glu Ser Gly Ala Glu Leu Ala Arg Pro Gly Ala Ser Val Lys
1               5                   10                  15

Leu Ser Cys Lys Ala Ser Gly Tyr Thr Phe Thr Ser Tyr Trp Met Gln
            20                  25                  30

Trp Val Lys Gln Arg Pro Gly Gln Gly Leu Glu Trp Ile Gly Ala Ile
        35                  40                  45

Tyr Pro Gly Asp Gly Asp Thr Arg Tyr Thr Gln Lys Phe Lys Gly Lys
    50                  55                  60

Ala Thr Leu Thr Ala Asp Lys Ser Ser Ser Thr Ala Tyr Met Gln Leu
65                  70                  75                  80

Ser Ser Leu Ala Ser Glu Asp Ser Ala Val Tyr Tyr Cys Ala Arg Gly
                85                  90                  95

Glu Tyr Gly Asn Tyr Phe Ala Tyr Trp Gly Gln Gly Thr Thr Val Thr
            100                 105                 110

Val Ser Ser Asn
        115

<210> SEQ ID NO 28
<211> LENGTH: 100
<212> TYPE: PRT
<213> ORGANISM: Mus musculus

<400> SEQUENCE: 28

Thr Ser Asp Ala Ser Leu Gly Glu Arg Val Thr Ile Thr Cys Lys Ala
1               5                   10                  15

Ser Gln Asp Ile Asn Ser Tyr Leu Ser Trp Phe Gln Gln Lys Pro Gly
            20                  25                  30

Lys Ser Pro Lys Thr Leu Ile Tyr Arg Ala Asn Arg Leu Val Asp Gly
        35                  40                  45

Val Pro Ser Arg Phe Ser Gly Ser Gly Ser Gly Gln Asp Tyr Ser Leu
    50                  55                  60

Thr Ile Ser Ser Leu Glu Tyr Glu Asp Met Gly Ile Tyr Tyr Cys Leu
65                  70                  75                  80

Gln Tyr Asp Glu Phe Pro Leu Thr Phe Gly Gly Gly Thr Lys Leu Glu
                85                  90                  95

Ile Lys Gln Lys

```
                100

<210> SEQ ID NO 29
<211> LENGTH: 108
<212> TYPE: PRT
<213> ORGANISM: Mus musculus

<400> SEQUENCE: 29

Ala Trp Leu Ser Gln Leu Ser Cys Thr Ala Ser Gly Phe Asn Ile Lys
1               5                   10                  15

Asp Thr Tyr Met His Trp Val Lys Gln Arg Pro Glu Gln Gly Leu Glu
            20                  25                  30

Trp Ile Gly Arg Ile Asp Pro Ala Asn Gly Asn Thr Lys Tyr Asp Pro
        35                  40                  45

Lys Phe Gln Gly Lys Ala Thr Ile Thr Ala Asp Thr Ser Ser Asn Thr
    50                  55                  60

Ala Tyr Leu Gln Leu Ser Ser Leu Thr Ser Glu Asp Thr Ala Val Tyr
65                  70                  75                  80

Tyr Cys Ala Arg Pro Ile His Tyr Tyr Gly Ser Ser Leu Ala Tyr
                85                  90                  95

Trp Gly Gln Gly Thr Thr Val Thr Val Ser Ser Lys
            100                 105

<210> SEQ ID NO 30
<211> LENGTH: 104
<212> TYPE: PRT
<213> ORGANISM: Mus musculus

<400> SEQUENCE: 30

Glu Phe His Ala Val Ser Leu Gly Gln Arg Ala Thr Ile Ser Cys Arg
1               5                   10                  15

Ala Ser Glu Ser Val Asp Ser Tyr Gly Asn Ser Phe Met His Trp Tyr
            20                  25                  30

Gln Gln Lys Pro Gly Gln Pro Pro Lys Leu Leu Ile Tyr Arg Ala Ser
        35                  40                  45

Asn Leu Glu Ser Gly Ile Pro Ala Arg Phe Ser Gly Ser Gly Ser Arg
    50                  55                  60

Thr Asp Phe Thr Leu Thr Ile Asn Pro Val Glu Ala Asp Asp Val Ala
65                  70                  75                  80

Thr Tyr Tyr Cys Gln Gln Ser Asn Glu Asp Pro Gly Arg Ser Glu Val
                85                  90                  95

Val Pro Ser Trp Arg Ser Asn Lys
            100

<210> SEQ ID NO 31
<211> LENGTH: 109
<212> TYPE: PRT
<213> ORGANISM: Mus musculus

<400> SEQUENCE: 31

Pro Arg Ala Ser Leu Gly Val Ser Glu Thr Leu Leu Cys Thr Ser Gly
1               5                   10                  15

Phe Thr Phe Thr Asp Tyr Tyr Met Ser Trp Val Arg Gln Pro Pro Gly
            20                  25                  30

Lys Ala Leu Glu Trp Leu Gly Phe Ile Arg Asn Lys Ala Asn Gly Tyr
        35                  40                  45

Thr Thr Glu Tyr Ser Ala Ser Val Lys Gly Arg Phe Thr Ile Ser Arg
    50                  55                  60
```

```
Asp Asn Ser Gln Ser Ile Leu Tyr Leu Gln Met Asn Thr Leu Arg Ala
 65                  70                  75                  80

Glu Asp Ser Ala Thr Tyr Tyr Cys Ala Arg Ala Asn Trp Ala Phe Asp
                 85                  90                  95

Tyr Trp Gly Gln Gly Thr Thr Val Thr Val Ser Ser Lys
            100                 105
```

<210> SEQ ID NO 32
<211> LENGTH: 94
<212> TYPE: PRT
<213> ORGANISM: Mus musculus

<400> SEQUENCE: 32

```
Ser Gly Asp Arg Val Ser Leu Ser Cys Arg Ala Ser Gln Ser Ile Ser
 1               5                  10                  15

Asn Tyr Leu His Trp Tyr Gln Gln Lys Ser His Glu Ser Pro Arg Leu
                20                  25                  30

Leu Ile Lys Tyr Ala Ser Gln Ser Ile Ser Gly Ile Pro Ser Arg Phe
             35                  40                  45

Ser Gly Ser Gly Ser Gly Thr Asp Phe Thr Leu Ser Ile Asn Ser Val
 50                  55                  60

Glu Thr Glu Asp Phe Gly Met Tyr Phe Cys Gln Gln Ser Asn Ser Trp
 65                  70                  75                  80

Pro Tyr Thr Phe Gly Gly Gly Thr Lys Leu Glu Ile Lys Gln
                85                  90
```

<210> SEQ ID NO 33
<211> LENGTH: 111
<212> TYPE: PRT
<213> ORGANISM: Mus musculus

<400> SEQUENCE: 33

```
Pro Ala Cys Leu Pro Gly Gly Ser Leu Arg Leu Ser Cys Ala Thr Ser
 1               5                  10                  15

Gly Phe Thr Phe Thr Asp Tyr Tyr Met Ser Trp Val Arg Gln Pro Pro
                20                  25                  30

Gly Lys Ala Leu Glu Trp Leu Gly Phe Ile Arg Asn Lys Ala Asn Gly
             35                  40                  45

Tyr Thr Thr Glu Tyr Ser Ala Ser Val Lys Gly Arg Phe Thr Ile Ser
 50                  55                  60

Arg Asp Asn Ser Gln Ser Ile Leu Tyr Leu Gln Met Asn Thr Leu Arg
 65                  70                  75                  80

Ala Glu Asp Ser Ala Thr Tyr Tyr Cys Ala Arg Ala Pro Leu Leu Tyr
                 85                  90                  95

Tyr Ala Met Asp Tyr Trp Gly Gln Gly Thr Thr Val Thr Val Ser
            100                 105                 110
```

<210> SEQ ID NO 34
<211> LENGTH: 102
<212> TYPE: PRT
<213> ORGANISM: Mus musculus

<400> SEQUENCE: 34

```
Arg Leu Pro Phe Tyr Ser Leu Glu Gln Arg Ala Thr Ile Ser Tyr Arg
 1               5                  10                  15

Ala Ser Lys Asn Val Ser Thr Ser Gly Tyr Ser Tyr Met His Trp Asn
                20                  25                  30
```

-continued

```
Gln Gln Lys Pro Gly Gln Pro Pro Lys Leu Leu Ile Tyr Leu Val Ser
        35                  40                  45

Asn Leu Glu Ser Gly Val Pro Ala Arg Phe Ser Gly Ser Gly Ser Gly
 50                  55                  60

Thr Asp Phe Thr Leu Asn Ile His Pro Val Glu Glu Asp Ala Ala
65                  70                  75                  80

Thr Tyr Tyr Cys Gln His Ile Arg Glu Leu Thr Arg Ser Glu Leu Val
                85                  90                  95

Pro Ser Trp Lys Ser Asn
            100
```

<210> SEQ ID NO 35
<211> LENGTH: 101
<212> TYPE: PRT
<213> ORGANISM: Mus musculus

<400> SEQUENCE: 35

```
Val Ser Cys Lys Ala Ser Gly Tyr Thr Phe Thr Ser Tyr Trp Met His
 1               5                  10                  15

Trp Val Lys Gln Arg Pro Gly Gln Gly Leu Glu Trp Ile Gly Met Ile
                20                  25                  30

Asp Pro Ser Asn Ser Glu Thr Arg Leu Asn Gln Lys Phe Lys Asp Lys
            35                  40                  45

Ala Thr Leu Asn Val Asp Lys Ser Ser Asn Thr Ala Tyr Met Gln Leu
 50                  55                  60

Ser Ser Leu Thr Ser Glu Asp Ser Ala Val Tyr Tyr Cys Ala Arg Gly
65                  70                  75                  80

Leu Arg His Tyr Trp Tyr Phe Asp Val Trp Gly Gln Gly Thr Thr Val
                85                  90                  95

Thr Val Ser Ser Lys
            100
```

<210> SEQ ID NO 36
<211> LENGTH: 99
<212> TYPE: PRT
<213> ORGANISM: Mus musculus

<400> SEQUENCE: 36

```
Thr Ile Leu Trp Arg Glu Gly Pro Phe Ser Tyr Arg Ala Ser Lys Ser
 1               5                  10                  15

Val Ser Thr Ser Gly Tyr Ser Tyr Met His Trp Asn Gln Gln Lys Pro
                20                  25                  30

Gly Gln Pro Pro Arg Leu Leu Ile Tyr Leu Val Ser Asn Leu Glu Ser
            35                  40                  45

Gly Val Pro Ala Arg Phe Ser Gly Ser Gly Ser Gly Thr Asp Phe Thr
 50                  55                  60

Leu Asn Ile His Pro Val Glu Glu Asp Ala Ala Thr Tyr Tyr Cys
65                  70                  75                  80

Gln His Ile Arg Glu Leu Thr Arg Ser Glu Val Pro Ser Trp Arg
                85                  90                  95

Ser Asn Lys
```

<210> SEQ ID NO 37
<211> LENGTH: 330
<212> TYPE: PRT
<213> ORGANISM: Homo sapiens

<400> SEQUENCE: 37

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 38
<211> LENGTH: 106
<212> TYPE: PRT
<213> ORGANISM: Homo sapiens

<400> SEQUENCE: 38

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

```
Gly Asn Ser Gln Glu Ser Val Thr Glu Gln Asp Ser Lys Asp Ser Thr
    50              55              60

Tyr Ser Leu Ser Ser Thr Leu Thr Leu Ser Lys Ala Asp Tyr Glu Lys
65              70              75              80

His Lys Val Tyr Ala Cys Glu Val Thr His Gln Gly Leu Ser Ser Pro
                85              90              95

Val Thr Lys Ser Phe Asn Arg Gly Glu Cys
            100             105
```